United States Patent [19]

Miller

[11] 3,953,596
[45] Apr. 27, 1976

[54] 8-OXA-3-AZABICYCLO(3.2.1)OCTANE ANALGESIC COMPOSITIONS AND METHOD OF ALLEVIATING PAIN IN ANIMALS

[75] Inventor: Alfred D. Miller, Wilmington, Del.

[73] Assignee: ICI United States Inc., Wilmington, Del.

[22] Filed: July 12, 1974

[21] Appl. No.: 487,924

Related U.S. Application Data

[62] Division of Ser. No. 370,011, June 14, 1973, Pat. No. 3,856,783.

[52] U.S. Cl. .............................................. 424/248
[51] Int. Cl.². ...................................... A61K 31/535
[58] Field of Search ................ 424/248; 260/240 D, 260/244 R

[56] References Cited
OTHER PUBLICATIONS

Cope et al., I, J. Am. Chem. Soc., Vol. 77, pp. 393–396 (1955).
Cope et al., II, J. Am. Chem. Soc., Vol. 81, pp. 4577–4583 (1959).
Newth et al., J. Chem. Soc. pp. 155–158 (1948).
Khullar et al., J. of Pharm. Sciences, 56, 331 (1967).

Primary Examiner—Sam Rosen
Assistant Examiner—Allen J. Robinson

[57] ABSTRACT

Disclosed are compounds, having the following general formula, which are useful as analgesics in living animals.

(a)

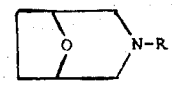

wherein R is a radical selected from the group consisting of aralkyl, aryl, aminoalkyl, arylalkanoyl, heteroaroyl, alkoxy substituted aroyl, alkenyl ($C_2$ to $C_4$), halogen substituted aralkyl, guanadinoalkyl, halogen substituted aroyl, alkyl substituted aroyl, halogen substituted arylalkanoyl, hexahydrobenzoyl, arylalkenoyl, o- or p-alkyl substituted phenylalkanoyl, alkyl substituted naphthylalkanoyl, alkanoyl ($C_3$ to $C_{20}$), haloalkyl substituted aroyl, alkoxy substituted aralkyl, heteroaralkyl, anilinocarbonyl, adamantanecarbonyl, arylsulfonyl, carboxyl substituted aroyl, hydroxyl substituted aroyl, alkanoyloxy substituted aroyl, arylglyoxylyl, alicyclic, arylene dicarbonyl-8-oxa-3-azabicyclo(3.2.1)octane, alkylene-8-oxa-3-azabicyclo(3.2.1)octane, alkylene dicarbonyl-8-oxa-3-azabicyclo(3.2.1)octane, and the pharmacologically acceptable acid addition salts thereof.

14 Claims, No Drawings

8-OXA-3-AZABICYCLO(3.2.1)OCTANE ANALGESIC COMPOSITIONS AND METHOD OF ALLEVIATING PAIN IN ANIMALS

This is a division, of application Ser. No. 370,011, filed June 14, 1973, now U.S. Pat. No. 3,856,783, issued Dec. 24, 1974.

This invention relates to 8-oxa-3-azabicyclo(3.2.1) octane compounds and to their methods of preparation and use.

The physiologically active compounds of the present invention are illustrated by the following general formula (a) 

wherein R is a radical selected from the group consisting of aralykl, aryl, aminoalkyl, arylalkanoyl, heteroaroyl, alkoxy substituted aroyl, alkenyl ($C_2$ to $C_4$), halogen substituted aralkyl, guanadinoalkyl, halogen substituted aroyl, alkyl substituted aroyl, halogen substituted arylalkanoyl, hexahydrobenzoyl, arylalkenoyl, o- and p-alkyl substituted phenylalkanoyl, alkyl substituted naphthylalkanoyl, alkanoyl ($C_3$ to $C_{20}$), haloalykl substituted aroyl, alkoxy substituted aralkyl, heteroaralkyl, anilinocarbonyl, adamantanecarbonyl, arylsulfonyl, carboxyl substituted aroyl, hydroxyl substituted aroyl, alkanoyloxy substituted aroyl, arylglyoxylyl, alicyclic, arylene dicarbonyl-8-oxa-3-azabicyclo (3.2.1) octane, alkylene-8-oxa-3-azabicyclo (3.2.1) octane, alkylene dicarbonyl-8-oxa-3-azabicyclo(3.2.1) octane, and the pharmacologically acceptable acid addition salts thereof.

For purposes of exemplification and not limitation, the above radicals designated R in relation to formula (a) include the following within their scope. The term "aralkyl" includes, for example, benzyl, phenethyl, α-methylphenethyl, o-, m-, and p-methylbenzyl, naphthylethyl, and phenylpropyl, wherein the alkyl portion of said radical is straight or branch chained and contains from 1 to 10 carbon atoms and the aryl portion is phenyl or naphthyl. Alkylene-8-oxa-3-azabicyclo(3.2.1) octane and alkylene dicarbonyl-8-oxa-3-azabicyclo(3.2.1) octane includes such radicals wherein the alkylene portion thereof contains from 1 to 10 carbon atoms. The term "aryl" by itself or in combination with other radicals is used herein to denote radicals, such as phenyl and naphthyl. Aminoalkyl represents an amine group substituted with 1 to 3 alkyl groups having from 1 to 10 carbon atoms. "Alkanoyl" as used herein by itself or in combination with other radicals includes such radicals having from 3 to 20 carbon atoms, for example, isobutyroyl, propionyl, caproyl, stearoyl, and heptanoyl. "Alkanoyl" when used herein in combination with other radicals includes such radicals having from 2 to 20 carbon atoms. Therefore, the term "arylalkanoyl" includes radicals, such as for example, phenylacetyl, phenylcaproyl, phenylstearoyl, and naphthylheptanoyl. The radical "heteroaroyl" includes, for example, nicotinoyl, thenoyl, and quinoxaloyl. When the term "alkyl" is used herein by itself or in combination with other radicals, it denotes both straight and branched chain alkyl radicals containing from 1 to 10 carbon atoms. For example, the alkyl portion of an alkyl substituted aroyl radical can contain from 1 to 10 carbon atoms and the aroyl radical can be substituted with at least 1 and no more than 5such alkyl groups, preferably 1 to 3. Further, for example, the alkyl portion of a guanadinoalkyl radical includes alkyl radicals containing from 1 to 10 carbon atoms. "Aroyl" as used herein by itself or in combination with other radicals includes unsubstituted radicals, for example, naphthoyl and benzoyl. "Haloalkyl substituted aroyl" radicals include aroyl radicals substituted with at least 1 and no more than 3 haloalkyl radicals each of which contains from 1 to 10 carbon atoms and at least 1 and no more than 6 halogen atoms. When halogen is referred to in relation to any of the radicals represented by R, all halogens are intended and thus fluorine, chlorine, iodine, and bromine are included; however, flourine, chlorine, and bromine are preferred. "Alkoxy substituted aroyl" as used herein includes aroyl radicals substituted with at least 1 and no more than 3 alkoxy groups which each contains from 1 to 10 carbon atoms and includes radicals, such as methoxybenzoyl, pentoxyben7oyl, and 3,5-dibutoxynaphthoyl. The radical "arylsulfonyl" includes, for example, benzenesulfonyl and naphthalenesulfonyl. For example, "alicyclic" includes cycloalkyl radicals having from 3 to 8 ring carbon atoms, such as cyclopropyl, cyclopentyl, cyclohexyl, and cycloheptyl. By "alkenyl" is included, for example, straight and branched chain radicals containing from 2 to 4 carbon atoms. The term "arylalkenoyl" as used herein includes radicals, such as cinnamoyl and other such radicals, wherein the alkenoyl portion of the radical contains from 3 to 10 carbon atoms. The term "alkanoyloxy substituted aroyl" as used herein includes radicals, such as acetoxybenzoyl and acetoxynaphthoyl, wherein the alakanoyloxy portion of the radicals contains from 2 to 10 carbon atoms and the aroyl radical is substituted with at least 1 and no more than 3 alkanoyloxy radicals. The terms "halogen substituted aralkyl, " "halogen substituted aroyl," and "halogen substituted arylalkanoyl" are used to indicate such radicals which are substituted with at least 1 and no more than 5 halogen atoms, preferably 1 to 3 halogen atoms. "Heteroaralkyl" includes, for example, radicals, such as thienylethyl, thienylhexyl, α-methylthienylethyl, and pyridylbutyl. "o- and p-Alkyl substituted phenylalkanoyl" includes radicals which are substituted with 1 to 3 ($C_1$ to $C_{10}$) alkyl radicals. "Alkyl substituted naphthylalkanoyl" radicals include such radicals substituted on the aromatic ring with up to 5 ($C_1$ to $C_{10}$) alkyl radicals. "Alkoxy substituted aralkyl" includes aralkyl radicals substituted with at least 1 and no more than 5 alkoxy groups ($C_1$ to $C_{10}$), preferably 1 to 3 such alkoxy groups. "Carboxyl substituted aroyl" and "hydroxyl substituted aroyl" includes aroyl radicals suitably substituted with at least 1 and no more than 5 carboxyl or hydroxyl groups, as the case may, preferably substituted with 1 to 3 of such groups.

Pharmacological studies indicate that the 8-oxa-3-azabicyclo(3.2.1) octane compounds of the present invention represented by formula (a) above are effective in alleviating pain in living animal bodies, more especially, mammalian bodies. In general, the present compounds exhibit analgesic and/or anti-inflammatory activity. Test results in laboratory animals indicate that all of the subject compounds have analgesic activity except where R in formula (a) above is phenylglyoxylyl, cyclohexyl or dimethoxyphenethyl and these compounds exhibit anti-inflammatory activity. As indicated many of the present compounds exhibit analgesic/antiinflammatory activity; and in addition, some of the present compounds also exhibit antipyretic activity. It has also been found that 8-oxa-3-azabicyclo(3.2.1)octane, 3-benzoyl-8oxa-3-azabicyclo(3.2.1)octane, 3-alkyl ($C_1$ to $C_6$)-8-oxa-3-azabicyclo(3.2.1)octane, and 3 acetyl-8-oxa-3-azabicyclo(3.2.1)octane are effective as analgesics when administered to living animals. Further, the pharmacologically acceptable acid addition salts of these compounds have also been found to have analgesic activity.

In a preferred subclass of the present invention, R in formula (a) above is selected from the group consisting of: phenyl; aminoalkyl ($C_1$ to $C_6$) where the amino group is primary, secondary, or tertiary; phenylacetyl; quinoxaloyl; mono-, di-, or tri-alkoxy ($C_1$ to $C_4$) substituted benzoyl; phenylalkyl where the alkyl constituent thereof contains from 1 to 4 carbon atoms such as benzyl, phenylpropyl, and phenethyl; alkenyl ($C_3$ and $C_4$); mono-, di-, or tri-halogen substituted phenylalkyl where the alkyl group contains from 1 to 4 carbon atoms and the halogen is substituted on the phenyl ring; guanadinoalkyl ($C_1$ to $C_4$); mono-, di-, or tri-halogen substituted benzoyl; mono-, di-, or tri-alkyl ($C_1$ to $C_4$) substituted benzoyl; mono-, di-, or trihalogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylalkanoyl wherein the alkanoyl group contains from 2 to 4 carbon atoms; o- and p-alkyl ($C_1$ to $C_4$) substituted phenylalkanoyl where the alkanoyl group contains 2 to 4 carbon atoms and the alkyl group is substituted on the phenyl ring; alkyl ($C_1$ to $C_4$) substituted naphthylalkanoyl where the alkanoyl group contains 2 to 4 carbon atoms and the alkyl group or groups, preferably 1 to 3 alkyl groups, are attached to the naphthyl ring; alkanoyl ($C_3$ to $C_{18}$); haloalkyl ($C_1$ to $C_4$) mono-, di-, or tri-substituted benzoyl wherein the haloalkyl group contains from 1 to 5 halogen atoms; mono-, di-, or tri-alkoxy ($C_1$ to $C_4$) substituted phenylalkyl wherein the alkyl group contains 1 to 4 carbon atoms and the alkoxy is substituted on the phenyl ring; thienylalkyl wherein the alkyl group contains from 1 to 4 carbon atoms; anilinocarbonyl; adamantanecarbonyl; phenylsulfonyl; mono- or di-carboxyl substituted benzoyl; mono- or di-hydroxyl substituted benzoyl; nicotinoyl; mono-or di-alkanoyloxy ($C_1$ to $C_4$) substituted benzoyl; thenoyl; phenylglyoxylyl; cycloalkyl ($C_4$ to $C_8$), terephtholoyl-8-oxa-3-azabicyclo(3.2.1)octane; alkylene ($C_1$ to $C_8$)-8-oxa-3-azabicyclo(3.2.1)octane; and alkylene ($C_1$ to $C_8$) dicarbonyl-8-oxa-3-azabicyclo(3.2.1)octane. When halogen is referred to in this subclass, all halogens are intended; however, fluorine, chlorine, and bromine are preferred. In this preferred subclass, the above radicals, representing R in formula (a) above, can be substituted suitably in any of the ortho, meta, or para positions on the ring or any combination thereof unless otherwise directly indicated. For example, ring structures of the present preferred species of substituent R in formula (a) may be substituted in two ortho positions or two meta positions and/or the para position, or one ortho and one para position or any desired position combinations thereof.

The terms "lower alkyl," "lower alkoxy," "lower haloalkyl," "lower alkanoyl," and "lower alkanoyloxy" can be used to describe such radicals as referred to above in the preceding paragraph when they contain up to four carbon atoms.

In another preferred subclass of the present invention R in formula (a) above is selected from the group consisting of: benzyl, phenyl, aminohexyl, phenylacetyl, quinoxaloyl, m-methoxybenzoyl, α-methylphenethyl, aminoethyl, propenyl, α-methyl p-chlorophenethyl, dimethylaminopropyl, phenethyl, 2-guanadinoethyl, p-chlorobenzoyl, p-toluoyl, m-chlorobenzoyl, o-chlorobenzoyl, o-toluoyl, m-chlorophenylacetyl, p-chlorophenylacetyl, m-toluoyl, ethylene-8-oxa-3-azabicyclo(3.2.1)octane, β-methylphenethyl, β,β-dimethylphenethyl, p-chlorophenethyl, hexahydrobenzoyl, o-chlorophenylacetyl, cinnamoyl, phenethylcarbonyl, o-methylphenylacetyl, heptnoyl, m-trifluoromethylbenzoyl, o-methoxyphenethyl, α-methylthienylethyl, anilinocarbonyl, adamantanecarbonyl, phenylsulfonyl, o-carboxybenzoyl, stearoyl, propanoyl, o-hydroxybenzoyl, nicotinoyl, o-acetoxybenzoyl, thenoyl, phenylglyoxylyl, cyclohexyl, 3,4-dimethoxyphenethyl, hexamethylene-8-oxa-3-azabicyclo(3.2.1)octane, adipyl-8-oxa-3-azabicyclo(3.2.1) octane, terephtholoyl-8-oxa-3-azabicyclo(3.2.1)octane, and the pharmacologically acceptable acid addition salts thereof.

Among the novel compounds of the present invention are, for example: 3-phenylacetyl-8-oxa-3-azabicyclo(3.2.1)octane; 3-(p-chlorobenzoyl)-8-oxa-3-azabicyclo(3.2.1)octane; 3-heptanoyl-8-oxa-3-azabicyclo(3.2.1)octane; 3-nicotinoyl-8-oxa-3-azabicyclo (3.2.1)octane; 3(m-chlorobenzoyl)-8-oxa-3-azabicyclo(3.2.1) octane; 3(o-chlorobenzoyl)-8-oxa-3-azabicyclo(3.2.1)octane; 3-(p-toluoyl)-8-oxa-3-azabicyclo(3.2.1)octane; 3-(m-chlorophenylacetyl)-8-oxa-3-azabicyclo(3.2.1)octane; 3-(o-chlorophenylacetyl)-8-oxa-3-azabicyclo(3.2.1)octane; 3-cinnamoyl-8-oxa-3-azabicyclo (3.2.1)octane; 3-(p-tolylacetyl)-8-oxa-3-azabicyclo(3.2.1)octane; 3-(p-chlorophenylacetyl)-8-oxa-3-azabicyclo(3.2.1)octane; 3-(o-tolylacetyl)-8-oxa-3-azabicyclo(3.2.1)octane; 3-(2-quinoxaloyl)-8-oxa-3-azabicyclo(3.2.1)octane; 3-(m-trifluoromethylbenzoyl)-8-oxa-3-azabicyclo(3.2.1)octane; 3-(α-thenoyl)-8-oxa-3-azabicyclo(3.2.1)octane; 3-heptanoyl-8-oxa-3-azabicyclo(3.2.1) octane; 3-hydrocinnamoyl-8-oxa-3-azabicyclo(3.2.1)octane; 3-(o-toluoyl)-8-oxa-3-azabicyclo(3.2.1)octane; 3-(m-toluoyl)-8-oxa-3-azabicyclo(3.2.1)octane; 3-hexahydrobenzoyl-8-oxa-3-azabicyclo(3.2.1)octane; 3-(m-methoxybenzoyl)-8-oxa-3-azabicyclo (3.2.1)octane; 3-stearoyl-8-oxa-3-azabicyclo(3.2.1)octane; 3-propionyl-8-oxa-3-azabicyclo(3.2.1)octane; 3-nicotinoyl-8-oxa-3-azabicyclo(3.2.1)octane; 3-(acetylsalicyloyl)-8-oxa-3-azabicyclo(3.2.1)octane; 3-(o-carboxybenzoyl)-8-oxa-3-azabicyclo (3.2.1)octane; 3-(1-adamantanecarbonyl)-8-oxa-3-azabicyclo(3.2.1) octane; 3-(phenylglyoxylyl)-8-oxa-3-azabicyclo(3.2.1)octane; 3-(o-hydroxybenzoyl)-8-oxa-3-azabicyclo(3.2.1)octane; 3-benzenesulfonyl-8-oxa-3-azabicyclo(3.2.1)octane; 3-(N-phenylcarbamoyl)-8-oxa-3-azabicyclo(3.2.1)octane; 3-allyl-8-oxa-3-azabicyclo (3.2.1)octane hydrochloride; 3-cyclohexyl-8-oxa-3-azabicyclo (3.2.1)octane hydrochloride; 3-phenyl-8-oxa-3-azabicyclo(3.2.1) octane; 3-phenyl-8-oxa-3-azabicylo(3.2.1)octane hydrochloride; 3-(p-chlorophenethyl)-8-oxa-3-azabicyclo(3.2.1)octane hydrochloride; 3-(α-methylphenethyl)-8-oxa-3-azabicyclo(3.2.1)octane hydrochloride; 3-(α-methylphenethyl)-8-oxa-3-azabicyclo(3.2.1) octane; 3-(3,4-dimethoxyphenethyl)-8-oxa-3-azabicyclo(3.2.1) octane;

3-(3,4-dimethoxyphenethyl)-8-oxa-3-azabicyclo(3.2.1) octane hydrochloride; 3-benzyl-8-oxa-3-azabicyclo(3.2.1)octane hydrochloride; 3-phenethyl-8-oxa-3-azabicyclo(3.2.1)octane hydrochloride; 3-(p-chlorophenethyl)-8-oxa-3-azabicylo(3.2.1) octane hydrochloride; 3-(p-methoxyphenethyl)8-oxa-3-azabicyclo (3.2.1)octane hydrochloride; 3-(α,α-dimethylphenethyl)-8-oxa-3-azabicyclo(3.2.1)octane hydrochloride; 3-(β-methylphenethyl)-8-oxa-3-azabicyclo(3.2.1)octane hydrochloride; 3-(α-methyl-p-chlorophenethyl)-8-oxa-3-azabicyclo(3.2.1)octane hydrochloride; 3-[1-(2-thienyl)isopropyl]-8-oxa-3-azabicyclo(3.2.1)octane hydrochloride; 3-(3-dimethylaminopropyl)-8-oxa-3-azabicyclo (3.2.1)octane dihydrochloride; 3-(2-aminoethyl)-8-oxa-3-azabicyclo(3.2.1)octane dihydrochloride; 3,3'-ethylene-bis [8-oxa-3-azabicyclo(3.2.1)octane]; 3-(6-aminohexamethylene)-8-oxa-3-azabicyclo(3.2.1)octane; 3,3'-hexamethylene-bis[8-oxa-3-azabicyclo(3.2.1)octane]; 3-(2-guanadinoethyl)-8-oxa-2-azabicyclo(3.2.1)octane hydrosulfate monohydrate; and the pharmacologically acceptable acid addition salts of such basic compounds.

The immediate precursor for making most of the novel compounds of the present is 8-oxa-3-azabicyclo(3.2.1) octane. This compound can be readily prepared by a two-step process as illustrated in the following Examples 1 and 2, starting with cis-2,5-bis-(hydroxymethyl)tetrahydrofuran. The compound cis-2,5-bis-(hydroxymethyl)tetrahydrofuran is prepared by the method disclosed in U.S. Pat. No. 3,040,062 or by methods disclosed by Newth and Wiggins, Research, London, Vol. 3, Supplement 3-1, pages 50–51 (1950); Turner et al., Analytical Chemistry, 26, 898–901 (1954); or Cope and Baxter, Journal American Chemical Society, 77, 393–396 (1955). Using cis-2,5-bis-(hydroxymethyl) tetrahydrofuran as the starting material, the ditosylate thereof is prepared by reaction with p-toluenesulfonyl chloride in pyridine. The resulting compound, cis-2,5-bis-(tosyloxymethyl) tetrahydrofuran, represented hereinafter by formula (II), can then be reacted with an ammonia-alcohol solution under pressure, as illustrated in Example 2, to form 8-oxa-3-azabicyclo(3.2.1) octane, represented hereinafter by formula (III). All of the novel compounds of the present invention, as well as those utilized in the claimed method of treatment, are cis isomers. Compound (III), in turn, can be converted to the hydrochloride salt as shown in Example 3, which as indicated can also be used as a precursor in making other compounds of the present invention. The acetate salt of 8-oxa-3-azabicyclo(3.2.1)octane can be prepared as illustrated in Example 4. Example 4 illustrates another method of preparing 8-oxa-3-azabicyclo(3.2.1)octane, i.e. reaction of cis-2,5-bis-(tosyloxymethyl)tetrahydrofuran with benzylamine to give 3-benzyl-8-oxa-3-azabicyclo(3.2.1)octane which can then be debenzylated to yield the parent compound.

While the above-described process involves the reaction of cis-2,5-bis-(tosyloxymethyl)tetrahydrofuran with an amine (in this case, ammonia) to give 8-oxa-3-azabicyclo (3.2.1)octane, it will be recognized by those skilled in the present art that the tosyloxy groups can be replaced by other sulfonate-bearing groups (e.g., methanesulfonyloxy) and halogens (e.g., chlorine) and the same product (III) will be obtained.

The various reactions and processes discussed above and more particularly described in following Examples 1 to 4.

EXAMPLE 1 cis-2,5-Bis-(Tosyloxymethyl)Tetrahydrofuran

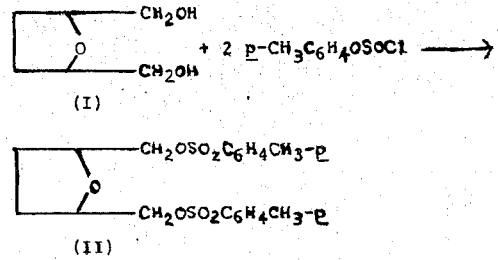

To a three-neck flask equipped with a thermometer, reflux condenser, mechanical stirrer, and dropping funnel a solution of 924 grams (7 moles) of cis-2,5-bis-(hydroxymethyl) tetrahydrofuran, represented by formula (I), in 900 ml of pyridine was placed and cooled at 5° C. A solution of 2669 grams (14 moles) of p-toluenesulfonyl chloride in 4 liters of pyridine was added slowly through the dropping funnel. The temperature during the addition was kept below 10°–15° C. After the addition of p-toluenesulfonyl chloride, the reaction mixture was stirred for 2 hours and then let stand at room temperature overnight. The reaction mixture was poured over ice-water and the product precipitated. The ditosylate, represented by formula (II), was filtered off and washed several times with water and dried. The product obtained had a melting point of 125°–126.5° C.

EXAMPLE 2

8-Oxa-3-Azabicyclo(3.2.1)Octane

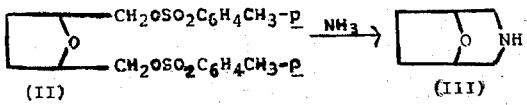

cis-2,5-Bis-(tosyloxymethyl)tetrahydrofuran, represented by formula (II), (500 grams, 1.135 moles) and 250 grams liquid ammonia in 2 liters of absolute ethanol were heated at 150° C. for 1.5–2 hours at 600–650 psig. The reaction mixture was cooled and treated with a methanolic sodium hydroxide solution (65 grams NaOH in 300 ml of methanol). The salt was filtered off and washed with ether. The filtrate and ethereal washings were combined and the solvents were stripped at atmospheric pressure. The product 8-oxa-3-azabicyclo(3.2.1)octane, represented by formula (III), was distilled at 177.5° C.

EXAMPLE 3

8-Oxa-3-Azabicyclo(3.2.1)Octane Hydrochloride (IV)

As soon as the product represented by formula (III) was distilled, it was dissolved in diethyl ether and NCl gas bubbled through slowly. The product 8-oxa-3-azabicyclo(3.2.1)octane hydrochloride had a melting point of 202°–204° C. and is very stable.

Analysis for $C_6H_{12}NOCl$. Calculated: C, 48.16%; H, 8.09%; N, 9.36%; Cl, 23.70%. Found: C, 47.95%; H, 8.06%, N, 9.45%; Cl, 23.50%.

EXAMPLE 4

8Oxa-3-azabicyclo( 3.2.1)Octane Hydroacetate

A mixture of 30 grams (0.015 mole) of N-benzyl-8-oxa-3-azabicyclo(3.2.1)octane, 1.0 gram of 10% palladium on charcoal, and 225 ml of glacial acetic acid was shaken in a Parr low pressure hydrogenator at 55° C. and an initial hydrogen pressure of 80 psig. Within 30 minutes the hydrogen uptake was complete. The catalyst was removed by filtration and the solvent removed on a rotary evaporator. The residue was diluted with ethyl acetate and cooled. The product 8-oxa-3-azabicyclo (3.2.1)octane hydroacetate was collected by filtration, washed with ethyl acetate and dried over $P_2O_5$ to obtain a white solid, having a melting point of 132°–133° C.

All of the other compounds within the scope of the present invention, represented by formula (a) above, can be prepared in accordance with the principles and processes illustrated in the following Examples 5 to 56, with particular reference to types of reactions, types of reactants, ratios of reactants, reaction solvents, reaction times, temperatures, and other conditions cited. The compounds, represented by formula (a) above where R is an acyl or substituted acyl radical, are readily prepared by reacting 8-oxa-3-azabicyclo(3.2.1)octane hydrochloride with an equal mole portion of an acyl chloride corresponding to the R substituent desired in a suitable solvent, such as an aqueous sodium hydroxide solution or benzene or other indicated solvents as illustrated in Examples 5 to 35. When substituent R of the compounds represented by formula (a) above is other than acyl, the subject compounds can be prepared by reacting the ditosylate compound represented by formula (II) with an excess of an amine corresponding to the R substituent desired in a suitable solvent, such as triethylene glycol dimethyl ether as illustrated in Examples 36 to 56.

EXAMPLE 5

3-Phenylacetyl-8-Oxa-3-Azabicyclo(3.2.1)Octane

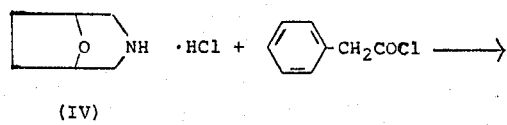

(IV)

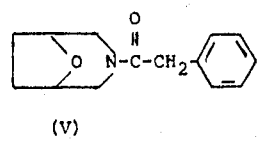

(V)

Phenylacetyl chloride (15.46 grams, 0.1 mole) (Aldrich Chemical Co., Inc., Milwaukee, Wisconsin) was slowly added to a mixture of 8-oxa-3-azabicyclo(3.2.1)octane hydrochloride (product of Example 3) (14.96 grams, 0.1 mole) and sodium hydroxide (10 grams) in 300 ml water at 10° C. After the addition of phenylacetyl chloride, the reaction mixture was stirred at room temperature for 2 hours. The crystalline solid (22.1 grams, 95.6%) which separated was filtered off, washed with water, and finally recrystallized from a blend of about 30% petroleum ether (boiling point 30°–60° C.) and 70% diethyl ether (v/v) to yield the product 3-phenylacetyl-8-oxa-3-azabicyclo(3.2.1)octane which had a melting point of 106°–106.5° C.

Analysis for $C_{14}H_{17}NO_2$. Calculated: C, 72.70%; H, 7.41%; N, 6.06%. Found: C, 72.50%; H, 7.69%; N, 6.16%.

EXAMPLE 6

3-(p-Chlorobenzoyl)-8-Oxa-3-Azabicyclo(3.2.1)Octane

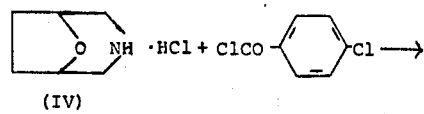

(IV)

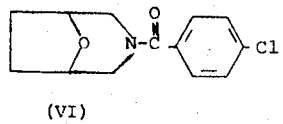

(VI)

p-Chlorobenzoyl chloride (0.07 mole, 12.26 grams) (Aldrich Chemical Co., Inc., Milwaukee, Wisc.) was slowly added to a mixture of 8-oxa-3-azabicyclo(3.2.1)octane hydrochloride (0.07 mole, 10.5 grams) and sodium hydroxide (7 grams) in 250 ml of water, at 10° C. After the addition of p-chlorobenzoyl chloride, the reaction mixture was stirred at room temperature for 2 hours and then let stand at room temperature overnight. The product which separated as a solid (17.5 grams, 100% yield) was filtered off, washed with water, and finally crystallized from a blend of about 30% petroleum ether (boiling point 30°–60° C.) and 70% diethyl ether (v/v). The product 3-(p-chlorobenzoyl)-8-oxa-3-azabicyclo(3.2.1)octane had a melting point of 110°–111° C.

Analysis for $C_{13}H_{14}O_2NCl$. Calculated: C, 62.03%, H, 5.60%; N, 5.56%; Cl, 14.08%. Found: C, 62.15%; H, 5.50%; N, 5.39%; Cl, 14.05%.

Using the procedure of Examples 5 and 6, 0.1 mole portions of 8-oxa-3-azabicyclo(3.2.1)octane hydrochloride [Compound (IV)] were reacted with 0.1 mole portions of other acyl chlorides listed in Table I below in aqueous sodium hydroxide solution to produce the 3-acyl-8-oxa-3-azabicyclo (3.2.1)octanes corresponding to the acyl radicals listed under the heading R in Table I.

TABLE I

3-Acyl-8-Oxa-3-Azabicyclo(3.2.1)Octanes

| Ex. | Acyl Chlorides | R | M.P. °C. | Found C | Found H | Found N | Found Cl or S | Calculated C | Calculated H | Calculated N | Calculated Cl or S | Crystallized From |
|---|---|---|---|---|---|---|---|---|---|---|---|---|
| 7 | m-Chlorobenzoyl chloride* | (m-Cl-C₆H₄-CO-) | 81–82 | 61.94 | 5.43 | 5.36 | 14.20 | 62.03 | 5.60 | 5.56 | 14.08 | 30% Petroleum ether (boiling point 30–60°C)-70% Diethyl ether (v/v).**** |
| 8 | o-Chlorobenzoyl chloride* | (o-Cl-C₆H₄-CO-) | 95–96 | 61.88 | 5.61 | 5.45 | 14.08 | 62.03 | 5.60 | 5.56 | 14.08 | do |
| 9 | p-Toluoyl chloride* | (p-CH₃-C₆H₄-CO-) | 79–80 | 72.55 | 7.21 | 6.01 | — | 72.69 | 7.41 | 6.05 | — | do |
| 10 | m-Chlorophenyl-acetyl chloride | (m-Cl-C₆H₄-CH₂-CO-) | 97–98 | 63.45 | 6.13 | 5.24 | — | 63.27 | 6.07 | 5.26 | — | do |
| 11 | o-Chlorophenyl-acetyl chloride | (o-Cl-C₆H₄-CH₂-CO-) | 123–125 | 63.45 | 6.13 | 5.18 | — | 63.27 | 6.07 | 5.26 | — | do |
| 12 | Cinnamoyl chloride | (C₆H₅-CH=CH-CO-) | 103–104 | 73.93 | 6.85 | 5.70 | — | 74.04 | 7.04 | 5.75 | — | do |
| 13 | p-Tolylacetyl chloride | (p-CH₃-C₆H₄-CH₂-CO-) | 124–125 | 73.70 | 7.87 | 5.70 | — | 73.44 | 7.80 | 5.70 | — | do |
| 14 | p-Chlorophenyl-acetyl chloride | (p-Cl-C₆H₄-CH₂-CO-) | 129–130 | 63.25 | 5.99 | 5.18 | — | 63.27 | 6.07 | 5.26 | — | 50% Ethanol-50% Diethyl ether (v/v). |
| 15 | o-Tolylacetyl chloride | (o-CH₃-C₆H₄-CH₂-CO-) | 138–140 | 73.52 | 7.78 | 5.63 | — | 73.44 | 7.80 | 5.70 | — | 30% Petroleum ether (boiling point 30–60°C)-70% Diethyl ether (v/v). |
| 16 | 2-Quinoxaloyl chloride* | (quinoxalin-2-yl-CO-) | 137–139 | 66.72 | 5.64 | 15.28 | — | 66.89 | 5.61 | 15.59 | — | 50% Methylene chloride-50% Diethyl ether (v/v). |
| 17 | Benzoyl chloride* | C₆H₅C(O)— | 49–51 | 71.70 | 6.64 | 6.71 | — | 71.90 | 6.92 | 6.46 | — | Diethyl ether |
| 18 | m-Trifluoromethyl benzoyl chloride** | (m-CF₃-C₆H₄-CO-) | 115–116 | 59.21 | 4.63 | 4.85 | — | 58.94 | 4.95 | 4.90 | — | Diethyl ether |
| 19 | α-thenoyl chloride*** | (2-thienyl-CO-) | 78–80 | 59.32 | 5.82 | 6.32 | 14.50 | 59.17 | 5.87 | 6.27 | 14.36 | Diethyl ether |

*Aldrich Chemical Co., Inc., Milwaukee, Wisconsin
**Pierce Chemical Co., Rockford, Illinois
***J. T. Baker Chemical Co., Phillipsburg, New Jersey
****Products of Examples 7 to 13 were all crystallized from the combination of solvents.

EXAMPLE 20

3-Heptanoyl-8-Oxa-3-Azabicyclo(3.2.1)Octane

Heptanoyl chloride (14.86 grams, 0.1 mole) was slowly added to a mixture of 8-oxa-3-azabicyclo(3.2.1)octane hydrochloride product of Example 3 (14.96 grams, 0.1 mole) and sodium hydroxide (10 grams) in 300 ml water, at 10° C. After the addition of heptanoyl chloride, the reaction mixture was stirred for 2 hours and then left overnight at room temperature. The product was extracted from the reaction mixture with diethyl ether and treated with DARCO G60 (activated carbon) After the removal of the diethyl ether, the product 3-heptanoyl-8-oxa-3-azabicyclo (3.2.1)octane was obtained as a clear liquid.

Analysis for $C_{13}H_{23}NO_2$. Calculated: C, 69.28%; H, 10.27%; N, 6.21%. Found: C, 69.33%; H, 10.41%; N, 6.16%.

Using the procedure of Example 20, 0.1 mole portions of 8-oxa-3-azabicyclo(3.2.1)octane hydrochloride [compound (IV)] were reacted with 0.1 mole portions of other acyl chlorides listed in Table II below in aqueous sodium hydroxide solution and extracting the reaction mixture with diethyl ether gave the 3-acyl-8-oxa-3-azabicyclo(3.2.1)octanes corresponding to the acyl radicals listed under the heading R in Table II.

a blend of about 30% petroleum ether (boiling point 30°–60° C.) and 70% diethyl ether (v/v) to white crystals having a melting point of 48°–49.5° C.

Analysis for $C_{12}H_{14}N_2O_2$. Calculated: C, 66.03%; H,

TABLE II

3-Acyl-8-Oxa-3-Azabicyclo(3.2.1)Octanes

| Ex. | Acyl Chlorides | R | M.P. °C. | Found C | Found H | Found N | Calculated C | Calculated H | Calculated N | Yield % | Crystallized From |
|-----|----------------|---|----------|---------|---------|---------|--------------|--------------|--------------|---------|-------------------|
| 21 | Hydrocinnamoyl chloride* | $C_6H_5CH_2CH_2\overset{O}{\underset{\|}{C}}-$ | Clear viscous liquid[1] | 73.39 | 7.61 | 5.70 | 73.44 | 7.80 | 5.70 | 98.5 | (2) |
| 22 | o-Toluoyl chloride** | (o-methylbenzoyl) | Colorless viscous liquid | 72.48 | 7.58 | 5.92 | 72.69 | 7.41 | 6.05 | 93.0 | — |
| 23 | m-Toluoyl chloride** | (m-methylbenzoyl) | Colorless viscous liquid | 72.89 | 7.46 | 6.05 | 72.69 | 7.41 | 5.93 | 97.0 | — |
| 24 | Hexahydrobenzoyl chloride*** | (cyclohexylcarbonyl) | 72–74 | 69.88 | 9.38 | 6.22 | 69.92 | 9.48 | 6.27 | 42.0 | 30% Petroleum ether (boiling point 30–60°C)-70% Diethyl ether (v/v). |
| 25 | m-Methoxybenzoyl chloride | (m-methoxybenzoyl) | 54.5–55.5 | 67.81 | 7.16 | 5.58 | 67.99 | 6.93 | 5.06 | 87.0 | do |
| 26 | Stearoyl chloride | $C_{17}H_{35}\overset{O}{\underset{\|}{C}}-$ | 51–53 | 75.80 | 11.81 | 3.59 | 75.93 | 11.95 | 3.69 | 80.0 | do |
| 27 | Propionyl chloride** | $C_2H_5\overset{O}{\underset{\|}{C}}-$ | Colorless liquid | 63.75 | 9.12 | 8.22 | 63.88 | 8.93 | 8.27 | 50.0 | do |

[1] On standing the product crystallized to soft white crystals.
[2] Purified by column chromatography (alumina/diethyl ether).
*Eastman Kodak Co., Rochester, N.Y.
**Aldrich Chemical Co., Inc., Milwaukee, Wisconsin
***K & K Laboratories, Inc., Plainview, N.Y.

EXAMPLE 28

3-Nicotinoyl-8-Oxa-3-Azabicyclo(3.2.1)Octane

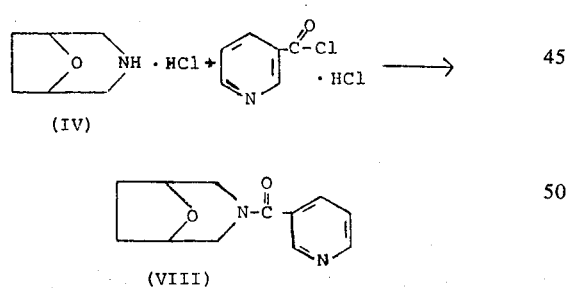

Nicotinoyl chloride hydrochloride (17.81 grams, 0.1 mole) was slowly added to a mixture of 8-oxa-3-azabicyclo(3.2.1) octane hydrochloride (15 grams, 0.1 mole) and sodium hydroxide (15 grams) in 300 ml of water, at 10° C. After the addition of nicotinoyl chloride hydrochloride, the reaction mixture was stirred for 2 hours and then left overnight at room temperature. The product was extracted from the reaction mixture with diethyl ether and the extract treated with DARCO G60 (activated carbon). After the removal of ether, the product was obtained as a clear liquid (10 grams, 46% yield) which crystallized. The product 3-nicotinoyl-8-oxa-3-azabicyclo(3.2.1)octane was recrystallized from 6.46%; N, 12.84%. Found: C, 66.05%; H, 6.44%; N, 12.66%.

EXAMPLE 29

3-(Acetylsalicyloyl)-8-Oxa-3-Azabicyclo(3.2.1)Octane

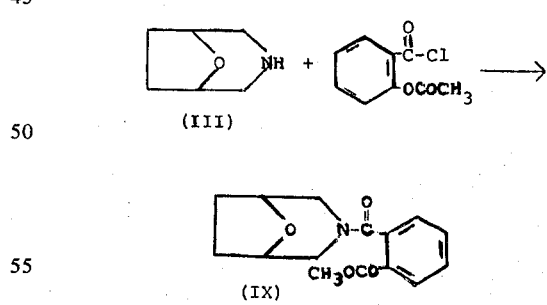

o-Acetoxybenzoyl chloride (0.1 mole, 19.85 grams) was slowly added to a mixture of 8-oxa-3-azabicyclo(3.2.1)octane (0.1 mole, 11.13 grams) and triethylamine (0.1 mole) in 60 ml of benzene at 20° C. The reaction mixture was stirred 2.5 hours at 25° C. The salt was filtered off and washed with benzene. After removal of benzene, the product was obtained as a viscous liquid which was purified by column chromatography (alumina). Impurities were eluted with ether and the product with methanol to yield the product represented by formula (IX).

Analysis for C₁₅H₁₇NO₄. Calculated: C, 65.44%; H, 6.23%; N, 5.09%. Found: C, 65.55%; H, 6.05%; N, 5.05%.

EXAMPLE 30

3-(o-Carboxybenzoyl)-8-Oxa-3-Azabicyclo(3.2.1)Octane

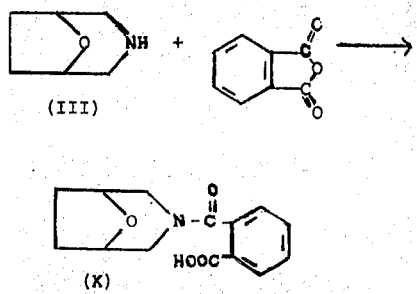

A solution of 11.3 grams (0.1 mole) 8-oxa-3-azabicyclo (3.2.1)octane in 20 ml of benzene was added to a suspension of 14.8 grams (0.1 mole) of phthalic anhydride in 50 ml of benzene at 8° C. The reaction mixture was stirred for 1 hour and then left overnight at room temperature. The product, 20.0 grams which separated, was filtered off and recrystallized from benzene ethanol. The product represented by formula (X) had a melting point of 149°–150.5° C.

Analysis for C₁₄H₁₅NO₄. Calculated: C, 64.36%; H, 5.79%; N, 5.36%. Found: C, 64.38%; H, 5.85%; N, 5.24%.

EXAMPLE 31

3-(1-Adamantanecarbonyl)-8-Oxa-3-Azabicyclo(3.2.1)Octane

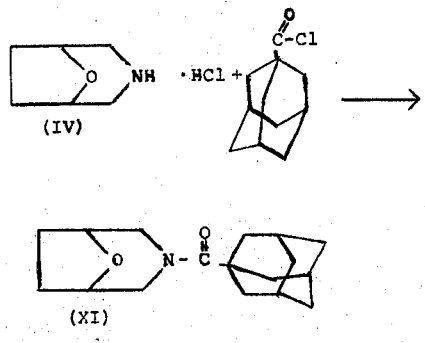

1-Adamantanecarbonyl chloride (19.87 grams, 0.1 mole, pulverized) (Aldrich Chemical Co., Inc., Milwaukee, Wisc.) was added to a mixture of 8-oxa-3-azabicyclo(3.2.1)octane hydrochloride (14.96 grams, 0.1 mole) and sodium hydroxide (10 grams) in 300 ml water. The reaction mixture was heated at 30° C. for 3 hours and then left overnight at room temperature. The product (22 grams) was filtered off, washed with water, and finally recrystallized from a blend of about 30% petroleum ether (boiling point 30°–60° C.) and 70% diethyl ether (v/v). The product had a melting point of 134°–136° C.

Analysis for C₁₇H₂₅NO₂. Calculated: C, 74.14%; H, 9.15%; N, 5.08%. Found: C, 74.10%; H, 9.21%; N, 5.06%.

EXAMPLE 32

3-(Phenylclyoxlyl)-8-Oxa-3-Azabicyclo(3.2.1)Octane

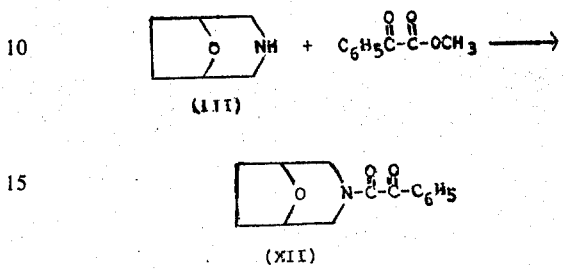

A 250 ml three-neck flask was fitted with a dropping funnel, a mechanical stirrer, and an 8 inch reflux condenser terminating in a still head. The still head carried a thermometer and was connected to a condenser set for downward distillation.

In the flask was placed 25 grams (0.152 mole) of methyl benzoyl formate and 25 ml xylene and the mixture was heated at 130° C. Then, the reactant represented by formula (III) (17.0 grams, 0.15 mole) was added slowly (in 16 minutes) through the dropping funnel and the reaction mixture was heated at 133°–134° C. for 1 hour. After removing the xylene under reduced pressure, 27.0 grams of a viscous liquid were obtained. The viscous liquid was extracted with diethyl ether, leaving behind a small amount of dark solid. Cooling the ethereal extract resulted in precipitation of 4.0 grams of the product represented by formula (XII). 3-Phenylglyoxylyl-8-oxa-3-azabicyclo (3.2.1)octane after recrystallization from ether had a melting point of 78°–79° C.

Analysis for C₁₄H₁₅N₁O₃. Calculated: C, 68.55%; H, 6.16%; N, 5.70%. Found: C, 68.47%; H, 6.21%; N, 5.66%.

EXAMPLE 33

3-(o-Hydroxybenzoyl)-8-Oxa-3-Azabicyclo(3.2.1)Octane

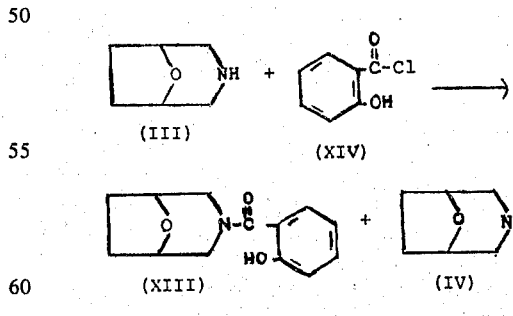

Salicylyl chloride (24 grams, 0.15 mole) was slowly added to a solution of 17.0 grams (0.15 mole) of the compound represented by formula (III) in 25 ml of benzene at 10° C. The reaction mixture was stirred for 1 hour and then left overnight at room temperature. The HCl salt of the compound represented by formula (III) illustrated by formula (IV) was filtered and the benzene solution was concentrated to dryness. The product represented by formula (XIII) (6.0 grams) crystallized on standing and was recrystallized for ethanol-diethyl ether (1:1). The product had a melting point of 155°–157° C.

Analysis for $C_{13}H_{15}O_3N_1$. Calculated: C, 66.93%; H, 6.48%; N, 6.00%. Found: C, 67.25%; H, 6.49%; N, 6.07%.

EXAMPLE 34

3-Benzenesulfonyl-8-Oxa-3-Azabicyclo(3.2.1)Octane

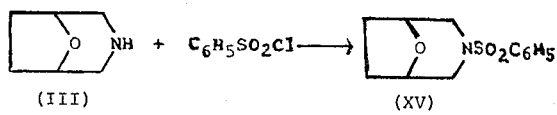

Benzenesulfonyl chloride (17.7 grams, 0.1 mole) dissolved in 15 ml of pyridine was slowly added to a solution of the compound represented by formula (III) in 15 ml of pyridine at 5° C. The reaction mixture was stirred for 2.5 hours at 5° C. and then poured over an ice-water mixture which effected a precipitate. The crude product was filtered off and washed with water many times to remove excess pyridine and pyridine hydrochloride. The product 3-benzenesulfonyl-8-oxa-3-azabicyclo (3.2.1)octane recrystallized from ethanol had a melting point of 166°–168° C.

Analysis for $C_{12}H_{15}N_3OS$. Calculated: C, 56.89%; H, 5.97%; N, 5.53%; S, 12.71%. Found: C, 56.83%; H, 5.82%; N, 5.52%; S, 12.83%.

EXAMPLE 35

3-(N-Phenylcarbamoyl)-8-Oxa-3-Azabicyclo(3.2.1)Octane

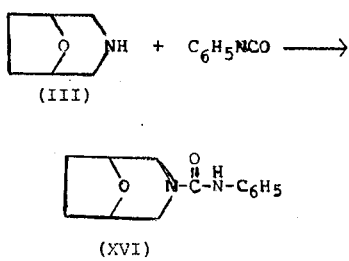

Phenyl isocyanate (11.9 grams, 0.1 mole) dissolved in 25 ml of benzene was slowly added to a solution of the compound represented by formula (III) (11.3 grams, 0.1 mole) in 25 ml of benzene at 0° C. The reaction mixture was stirred for 2 hours at 14°–16° C. and then left overnight at room temperature. The product, white crystals, was filtered off, washed with benzene, and recrystallized from ethanol. The product 3-(N-phenylcarbamoyl)-8-oxa-3-azabicyclo(3.2.1)octane had a melting point of 184°–186° C.

Analysis for $C_{13}H_{16}N_2O_2$. Calculated: C, 67.22%; H, 6.94%; N, 12.16%. Found: C, 67.45%; H, 7.01%; N, 12.06%.

EXAMPLE 36

3-Allyl-8-Oxa-3-Azabicyclo(3.2.1)Octane Hydrochloride

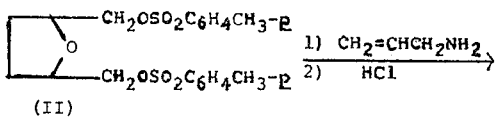

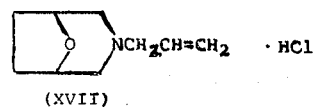

Allylamine (1.2 mole, 68.5 grams), 2,5-bis(tosyloxymethyl)tetrahydrofuran (0.4 mole, 176 grams), and 700 ml of absolute ethanol were charged into a one gallon autoclave and heated at 150° C. for 2 hours and 200 psig pressure. The reaction mixture was cooled and treated with a methanolic sodium hydroxide solution (0.8 mole, 32 grams/300 ml). The resulting tosylate salt was filtered and the excess allylamine and ethanol were stripped from the filtrate at atmospheric pressure. 3-Allyl-8-oxa-3-azabicyclo(3.2.1)octane distilled as a colorless liquid (terminal pot temperature 125° C./0.5 mm Hg). The product was dissolved in ether and anhydrous HCl bubbled in the solution. 3-Allyl-8-oxa-3-azabicyclo(3.2.1)octane hydrochloride, represented by formula (XVII), which precipitated as white crystals, was filtered and washed with ether. The product had a melting point of 169°–171° C.

Analysis for $C_9H_{16}NOCl$. Calculated: C, 56.98%; H, 8.50%; N, 7.40%; Cl, 18.69%. Found: C, 57.21%; H, 8.50%; N, 7.32%; Cl, 18.90%.

EXAMPLE 37

3-Cyclohexyl-8-Oxa-3-Azabicyclo(3.2.1)Octane Hydrochloride

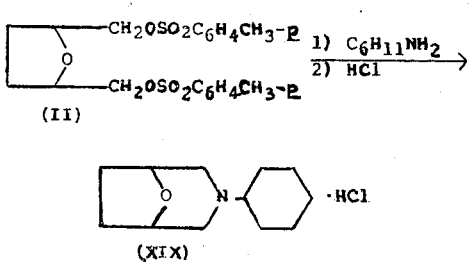

Cyclohexylamine (0.6 mole, 59.6 grams) was reacted with the ditosylate represented by formula (II) (0.2 mole, 88.1 grams) in 150 ml of Ansul 161 (triethylene glycol dimethyl ether at 180° C. for 2 hours. The reaction mixture was cooled to room temperature and neutralized with a methanolic sodium hydroxide solution (16 grams NaOH in 200 ml $CH_3OH$). Sodium tosylate was filtered off and the excess cyclohexylamine and Ansul 161 were stripped from the filtrate under aspirator pressure. 3-Cyclohexyl-8-oxa-3-azabicyclo(3.2.1)octane, identified herein as product (XVIII), was distilled under vacuum (terminal pot temperature 280° C./0.1 mm Hg).

Product (XVIII) (11.12 grams) was dissolved in 200 ml of ether and anhydrous hydrogen chloride was bubbled through the solution. The 3-cyclohexyl-8-oxa-3-azabicyclo(3.2.1)octane hydrochloride, represented by the formula (XIX), was filtered, washed with ether, and dried.

Analysis for $C_{12}H_{22}NOCl$. Calculated: C, 62.18%; H, 9.57%; N, 6.04%; Cl, 15.30%. Found: C, 61.74%; H, 9.54%; N, 6.09%; Cl, 15.47%.

EXAMPLE 38

3-Phenyl-8-Oxa-3-Azabicyclo(3.2.1)Octane

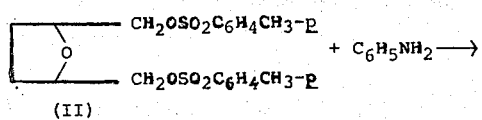

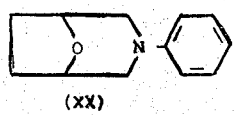

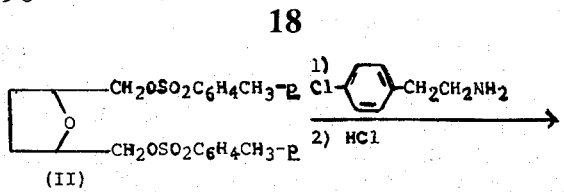

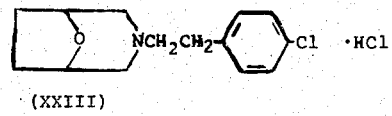

Aniline (1.2 mole, 111.8 grams) was added to a mixture of 2,5-bis(tosyloxymethyl)tetrahydrofuran, represented by formula (II), (0.4 mole, 176.2 grams) and 300 ml of Ansul 161 (triethylene glycol dimethyl ether) and the reaction mixture heated for 4 hours at 185° C. The reaction mixture was cooled to room temperature and neutralized with a methanolic sodium hydroxide solution (32 grams NaOH in 300 ml $CH_3OH$). Sodium tosylate was filtered and Ansul 161 and excess aniline stripped from the filtrate under aspirator pressure. 3-Phenyl-8-oxa-3-azabicyclo(3.2.1)octane, represented by formula (XX), was distilled at 113° C./0.15 mm Hg. The product solidified on standing and after recrystallization from methanol had a melting point of 84°–85° C.

Analysis for $C_{12}H_{15}NO$. Calculated: C, 76.15%; H, 7.99%; N, 7.40%. Found: C, 76.26%; H, 8.14%; N, 7.31%.

EXAMPLE 39

3-Phenyl-8-Oxa-3-Azabicyclo(3.2.1)Octane Hydrochloride

3-Phenyl-8-oxa-3-azabicyclo(3.2.1)octane, represented by formula (XX), (0.122 mole, 23 grams) was dissolved in diethyl ether and anhydrous hydrogen chloride was bubbled through the solution. The product 3-phenyl-8-oxa-3-azabicyclo(3.2.1)octane hydrochloride was filtered off, washed with diethyl ether, and dried. The product had a melting point of 168°–170° C.

Analysis for $C_{12}H_{16}NOCl$. Calculated: C, 63.85%; H, 7.15%; N, 6.21%; Cl, 15.71%. Found: C, 63.61%; H, 7.44%; N, 6.04%; Cl, 15.67%.

EXAMPLE 40

3-(p-Chlorophenethyl)-8-Oxa-3-Azabicyclo(3.2.1)Octane Hydrochloride p-Chlorophenethylamine (0.643 mole, 100 grams) was added to a mixture of 2,5-bis(tosyloxymethyl)tetrahydrofuran (0.214 mole, 99.6 grams) and 200 ml of Ansul 161 (triethylene glycol dimethyl ether) and stirred the reaction mixture for 3 hours at 180° C. The reaction mixture was cooled to room temperature and neutralized with a methanolic sodium hydroxide solution (0.429 mole, 17.14 grams NaOH in 200 ml $CH_3OH$) while stirring for 15 minutes. The solvents and excess starting amine were distilled from the reaction mixture under aspirator pressure. The residue was filtered collecting the sodium p-toluenesulfonate. The filtrate was distilled collecting one fraction (terminal pot temperature 280° C./0.1 mm Hg). The distillate which solidified was recrystallized from methanol obtaining 3-(p-chlorophenethyl)-8-oxa-3-azabicyclo(3.2.1)octane.

3-(p-Chlorophenethyl)-8-oxa-3-azabicyclo(3.2.-1)octane (0.133 mole, 32.6 grams) was dissolved in 2 liters of anhydrous diethyl ether and anhydrous hydrogen chloride was bubbled through solution to obtain a fine white precipitate. The precipitate was collected by filtration, washed with diethyl ether, and dried. The product obtained, 3-(p-chlorophenethyl)-8-oxa-3-azabicyclo(3.2.1)octane hydrochloride, represented by formula (XXIII), had a melting point of 194.5°–195.5° C.

Analysis for $C_{14}H_{19}NOCl_2$. Calculated: C, 58.34%; H, 6.64%; N, 4.86%; Cl, 24.61%. Found: C, 58.44%; H, 7.08%; N, 4.70%; Cl, 24.40%.

Using the procedure in the first paragraph of Example 40, 0.05 mole portions of 2,5-bis(tosyloxymethyl)tetrahydrofuran, represented by formula (II), is reacted with 0.15 mole portions of amines listed in Table III for 2 hours in triethylene glycol dimethyl ether to produce various compounds of the present invention corresponding to the aralkyl radicals listed under the heading R in Table III. In Examples 42 and 44 to 51, the 3-aralkyl-8-oxa-azabicyclo(3.2.1)octane compounds obtained by the above process were converted to their hydrochloride salts by bubbling anhydrous hydrogen chloride through an ethereal solution of said 3-aralkyl-8-oxa-azabicyclo(3.2.1)octane compounds by the process set forth in the second paragraph of Example 40.

TABLE III

3-Aralkyl-8-Oxa-3-Azabicyclo(3.2.1)Octane 

| | | | | ANALYSIS | | | | | | | |
|---|---|---|---|---|---|---|---|---|---|---|---|
| | | | | Found | | | | Calculated | | | |
| Ex. | Amine Reactant | R | B.P. or M.P. | C | H | N | Cl | C | H | N | Cl |
| 41 | α-Methylphenethyl amine | ⟨phenyl⟩-CH₂CH(CH₃)- | 120.5–120.8°C/ 0.44–0.46 mm Hg | 77.73 | 9.38 | 5.72 | — | 77.89 | 9.15 | 6.06 | — |
| 42 | α-Methylphenethyl amine | HCl·⟨phenyl⟩-CH₂CH(CH₃)- | 201.5–202°C | 67.39 | 8.46 | 5.40 | 13.43 | 67.27 | 8.28 | 5.23 | 13.24 |
| 43 | 3,4-Dimethoxy-phenethyl amine | CH₃O-⟨phenyl(OCH₃)⟩-CH₂CH₂- | 68.5–69°C | 69.24 | 8.44 | 5.05 | — | 69.28 | 8.36 | 5.05 | — |
| 44 | 3,4-Dimethoxy-phenethyl amine | HCl·CH₃O-⟨phenyl(OCH₃)⟩-CH₂CH₂- | 225–226°C | — | — | — | — | — | — | — | — |
| 45 | Benzyl amine | HCl·⟨phenyl⟩-CH₂- | 185–185.5°C | 65.08 | 7.30 | 5.78 | 14.57 | 65.13 | 7.57 | 5.84 | 14.79 |
| 46 | Phenethyl amine | HCl·⟨phenyl⟩-CH₂CH₂- | 217.5–219°C | — | — | — | 14.04 | — | — | — | 13.97 |
| 47 | p-Chlorophenethyl amine | HCl·Cl-⟨phenyl⟩-CH₂CH₂- | 194.5–195.5°C | 58.44 | 7.08 | 4.70 | 24.40 | 58.34 | 6.64 | 4.86 | 24.61 |
| 48 | p-Methoxyphenethyl amine | HCl·CH₃O-⟨phenyl⟩-CH₂CH₂- | 200–201°C | 63.25 | 7.79 | 4.76 | 12.59 | 63.48 | 7.82 | 4.94 | 12.94 |
| 49 | α,α-Dimethylphenethyl amine | HCl·⟨phenyl⟩-CH₂-C(CH₃)₂- | 244.5–245°C | 68.40 | 8.88 | 4.88 | 12.60 | 68.19 | 8.58 | 4.97 | 12.58 |
| 50 | β-Methylphenethyl amine | HCl·⟨phenyl⟩-CHCH₂- with CH₃ | 166–167°C | 67.43 | 8.37 | 5.12 | 13.09 | 67.27 | 8.28 | 5.23 | 13.24 |
| 51 | α-Methyl-p-chloro-phenethyl amine | HCl·Cl-⟨phenyl⟩-CH₂CH(CH₃)- | 205–205–207°C | 60.08 | 6.82 | 4.51 | 23.42 | 59.75 | 6.69 | 4.64 | 23.56 |

If desired, 3-benzyl-8-oxa-3-azabicyclo(3.2.1)octane can be debenzylated to form 8-oxa-3-azabicyclo(3.2.1)octane by dissolving the said benzyl derivative in absolute alcohol and then reacting same with hydrogen in the presence of a suitable amount of palladium on carbon (normally about 2% of 10% palladium or carbon based on the total weight of the reaction mixture is sufficient under pressure of about 70 psig and at about 70°–75° C.

EXAMPLE 52

3-[1-(2-Thienyl)Isopropyl]-8-Oxa-3-Azabicyclo(3.2.-1)Octane Hydrochloride

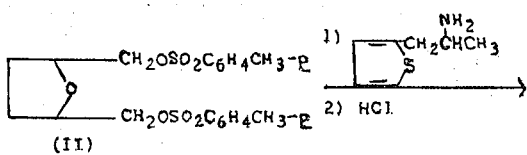

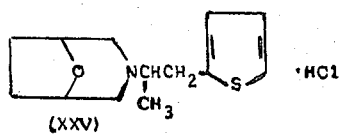

β-(2-Thienyl)isopropylamine (0.063 mole, 8.9 grams) was added to a mixture of 2,5-bis(tosyloxymethyl)tetrahydrofuran (0.063 mole, 27.7 grams) and tributylamine (0.126 mole, 23.3 grams) in 150 ml of Ansul 161 (triethylene glycol dimethyl ether). The reaction mixture was stirred for 3 hours at 185° C. and cooled to room temperature. Then a methanolic sodium hydroxide solution (0.126 mole, 5.03 grams NaOH in 125 ml CH₃OH) was added to the reaction mixture and stirred for 15 minutes.

Sodium p-toluenesulfonate was collected by filtration and the filtrate was stripped of solvents. The residue was distilled collecting one fraction (terminal pot temperature 290° C., vapor temperature 135° C./0.2 mm Hg). The distillate was placed on silica gel and eluted first with methylene chloride (impurity removed) and finally with diethyl ether to obtain the pure 3-[1-(2-thienyl)isopropyl]-8-oxa-3-azabicyclo(3.2.1) octane.

3-[1-(2-Thienyl)isopropyl]-8-oxa-3-azabicyclo(3.2.1) octane (4.77 grams) was dissolved in anhydrous diethyl ether and anhydrous hydrogen chloride was bubbled through the solution effecting a white crystalline precipitate. The precipitate was collected by filtration, washed with diethyl ether, and dried. The product 3-[1-(2-thienyl)isopropyl]-8-oxa-3-azabicyclo(3.2.1) octane hydrochloride represented by formula (XXV) had a melting point of 232.5°–233.5° C.

Analysis for $C_{13}H_{20}NOClS$. Calculated: C, 57.02%; H, 7.36%; N, 5.12%; S, 11.71%; Cl, 12.95%. Found: C, 57.13%; H, 7.40%; N, 5.04%; S, 11.61%; Cl, 12.96%.

EXAMPLE 53

3-Dimethylaminopropyl-8-Oxa-3-Azabicyclo(3.2.1)Octane Dihydrochloride

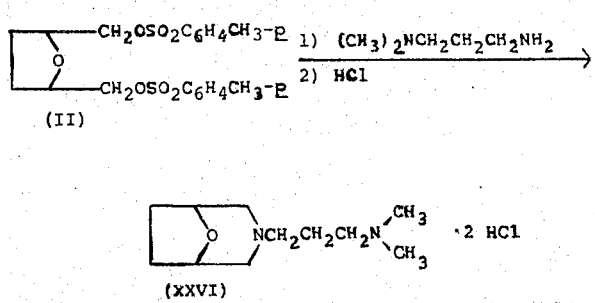

(II)

(XXVI)

Dimethylaminopropylamine (1.2 mole, 122.8 grams) was slowly added over 20 minutes to a mixture of 2,5-bis-(tosyloxymethyl)tetrahydrofuran and 300 ml of Ansul 161 (triethylene glycol dimethyl ether) while maintaining the reaction temperature between 155°–160° C. Continued heating for 2.5 hours after addition. Stripped solvent and excess dimethylaminopropylamine from reaction mixture under aspirator pressure (terminal pot temperature 150° C.). A methanolic sodium hydroxide solution (0.8 mole, 32 grams NaOH in 300 ml $CH_3OH$) was added to the pot residue which produced a precipitate. Filtered the tosylate salt and distilled the filtrate rapidly (terminal pot temperature 225° C.) collecting one fraction.

The distillate was dissolved in 2 liters of anhydrous diethyl ether and anhydrous hydrogen chloride was bubbled through the solution producing a precipitate. The precipitate was collected by filtration, washed with ether and neutralized with aqueous sodium hydroxide. The aqueous mixture was extracted with diethyl ether and the combined extracts stripped of diethyl ether. The residue was distilled and 3-dimethylaminopropyl-8-oxa-3-azabicyclo(3.2.1)octane was obtained.

3-Dimethylaminopropyl-8-oxa-3-azabicyclo(3.2.1)octane (0.038 mole, 7.5 grams) was dissolved in 1500 ml anhydrous diethyl ether and anhydrous hydrogen chloride was bubbled through the solution producing a white precipitate. The precipitate was collected by filtration, washed with diethyl ether, and dried. The product 3-dimethylaminopropyl-8-oxa-3-azabicyclo(3.2.1) octane dihydrochloride, represented by formula (XXVI), was obtained. It had a melting point of 252°–258° C.

Analysis for $C_{11}H_{23}N_2OCl$. Calculated: C, 48.71%; H, 8.92%; N, 10.33%; Cl, 26.14%. Found: C, 48.50%; H, 9.10%; N, 10.36%; Cl, 26.15%.

EXAMPLE 54

3-(2-Aminoethyl)-8-Oxa-3-Azabicyclo(3.2.1)Octane Dihydrochloride (XXXII)

and 3,3'-Ethylene-bis[8-Oxa-3-Azabicyclo (3.2.1)Octane] Dihydrochloride (XXXI)

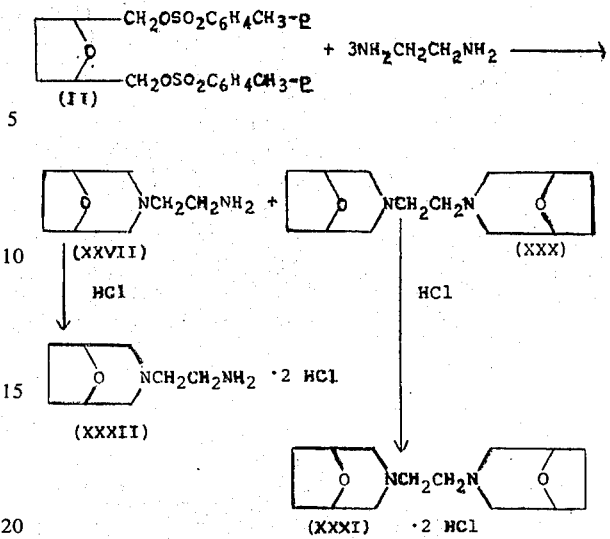

Ethylenediamine (3.0 moles, 180.3 grams) was reacted with the compound represented by formula (II) (1.0 mole, 440.5 grams) in 550 ml Ansul 141 (diethylene glycol dimethyl ether) at 152° C. for 2 hours. The Ansul 141 was stripped from the reaction mixture and a methanolic sodium hydroxide solution (2.0 moles, 80 grams NaOH in 500 ml $CH_3OH$) was added. The resulting mixture was stirred for 15 minutes at room temperature and the resulting tosylate salt was filtered off. Then the solvents were stripped and the residue was distilled very rapidly and one fraction was collected (terminal pot temperature 250° C., vapor temperature 210° C./0.1 mm Hg).

Solids crystallized from the distillate on standing were collected by filtration and recrystallized from diethyl ether, and then methanol. Upon drying, a white crystalline material having a melting point of 100.5°–101° C. was identified as 3,3'-ethylene-bis[8-oxa-3-azabicyclo (3.2.1)octane], represented by formula (XXX).

Analysis for $C_{14}H_{24}N_2O_2$. Calculated: C, 66.63%; H, 9.59%; N, 11.10%. Found: C, 66.70%; H, 10.04%; N, 11.10%.

The compound 3,3-ethylene-bis[8-oxa-3-azabicyclo(3.2.1) octane] dihydrochloride, represented by formula (XXXI), was prepared by dissolving the compound represented by formula (XXX) (0.7 grams, 0.0384 mole) in diethyl ether and bubbling in anhydrous hydrogen chloride. The product represented by formula (XXXI) had a melting point of 313° C.

Analysis for $C_{14}H_{26}N_2O_2Cl_2$. Calculated: C, 51.69%; H, 8.06%; N, 8.61%; Cl, 21.80%. Found: C, 51.58%; H, 8.00%; N, 8.43%; Cl, 21.77%.

The filtrate, from which the compound represented by formula (XXX) was isolated, was stripped of solvents and distilled collecting 81.7 grams of 3-(2-aminoethyl)-8-oxa-3-azabicyclo(3.2.1)octane (b.p. 68.5° C./0.07 mm Hg). 27 Grams of 3-(2-aminoethyl)-8-oxa-3-azabicyclo(3.2.1)octane were dissolved in 500 ml of anhydrous diethyl ether. Anhydrous hydrogen chloride was passed through the resulting ethereal solution to obtain a fine crystalline precipitate. The precipitate was filtered off, washed with anhydrous diethyl ether, and dried yielding 33.9 grams of 3-(2-aminoethyl)-8-oxa-3-azabicyclo (3.2.1)octane dihydrochloride, represented by formula (XXXII), having a melting point of 261.5°–262.5° C.

Analysis for C₈H₁₈N₂OCl₂. Calculated: C, 41.93%; H, 7.92%; N, 12.23%; Cl, 30.94%. Found: C, 42.05%; H, 8.21%; N, 12.23%; Cl, 30.91%.

EXAMPLE 55

3-(6-Aminohexamethylene)-8-Oxa-3-Azabicyclo(3.2.1)Octane (XXVIII)

and 3,3'-Hexamethylene-Bis[8-Oxa-3-Azabicyclo(3.2.1)Octane] (XXIX)

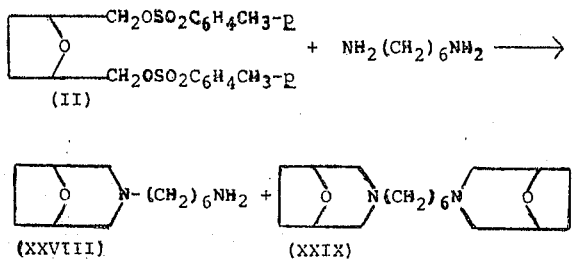

Hexamethylenediamine (0.4 mole, 46.5 grams) was reacted with the compound represented by formula (II) (0.4 mole, 176.2 grams) in 400 ml of Ansul 161 (triethylene glycol dimethyl ether) at 190° C. for 2 hours. The reaction mixture was cooled and treated with a methanolic sodium hydroxide solution (32 grams NaOH in 400 ml CH₃OH). The tosylate salt was filtered and after stripping the Ansul 161, the residue was distilled (terminal pot temperature 280° C., vapor temperature 230° C./0.1 mm Hg). Solids which formed in the distillate were collected by filtration and recrystallized from methanol/water. These solids were characterized as 3,3-hexamethylene-bis[8-oxa-3-azabicyclo(3.2.1)octane], represented by formula (XXIX).

The compound represented by formula (XXIX) (0.015 mole, 4.76 grams) was dissolved in 250 ml anhydrous diethyl ether and anhydrous hydrogen chloride was bubbled through the solution producing a precipitate. The precipitate started to coagulate, the diethyl ether was decanted and fresh anhydrous diethyl ether was added. The mixture triturated and the precipitate collected by filtration obtaining 3,3'-hexamethylene-bis[8-oxa-3-azabicyclo(3.2.1)octane] dihydrochloride having a melting point of 282°–283° C.

Analysis for C₁₈H₃₄N₂O₂Cl₂. Calculated: C, 56.68%; H, 8.99%; N, 7.35%; Cl, 18.59%. Found: C, 56.16%; H, 9.19%; N, 6.92%; Cl, 18.67%.

The filtrate, from which the compound represented by formula (XXIX) was isolated, was redistilled under reduced pressure collecting the 3-(6-aminohexamethylene-8-oxa-3-azabicyclo (3.2.1)octane, represented by formula (XXVIII) having a boiling point of 92.2° C./0.04 mm Hg. The dihydrochloride salt of (XXVIII) was prepared and had a melting point of 244°–245° C.

Analysis for C₁₂H₂₆NOCl₂. Calculated: C, 50.52%; H, 9.19%; N, 9.82%; Cl, 24.86%. Found: C, 50.42%; H, 9.27%; N, 9.90%; Cl, 24.61%.

EXAMPLE 56

3-(2-Guanadinoethyl)-8-Oxa-3-Azabicyclo(3.2.1)Octane Hydrosulfate Monohydrate

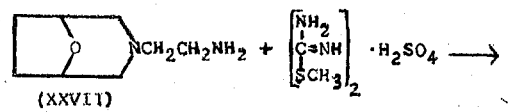

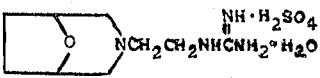

3-(β-Aminoethyl)-8-oxa-3-azabicyclo(3.2.1)octane (0.15 mole, 23.43 grams) was added to a mixture of 2-methyl-2-thiopseudourea sulfate (0.075 mole, 20.88 grams) in 70 ml water and an exothermic reaction was produced. Much bubbling occurred due to the evolution of methyl mercaptan. The reaction mixture was stirred for 2.75 hours at 85° C., and after cooling at room temperature concentrated hydrochloric acid (0.077 mole, 7.62 grams) was added and let stand for 17 hours 2.0 grams of yellowish solid was collected by filtration and the water was removed from the filtrate using a rotatory evaporator under aspirator pressure. 200 ml of methanol was added to the viscous residue which effected a white granular precipitate. Addition of more methanol effected another crop of the desired crystals of 3-(2-guanadinoethyl)-8-oxa-3-azabicyclo(3.2.1)octane hydrosulfate monohydrate.

Analysis for C₉H₂₂N₄O₆S. Calculated: C, 34.38%; H, 7.06%; N, 17.82%; S, 10.20%. Found: C, 34.22%; H, 6.88%; N, 17.62%; S, 10.52%.

The condensation-type products of the present invention, such as when R in formula (a) above is arylene dicarbonyl-8-oxa-3-azabicyclo(3.2.1)octane or alkylene dicarbonyl-8-oxa-3-azabicyclo(3.2.1)octane, can be prepared by reacting at 10° to 20° C. two moles of 8-oxa-3-azabicyclo(3.2.1)octane with one mole of the desired arylene or alkylene diacid chloride, such as terephtholoyl chloride or adipyl chloride in a solvent, such as benzene in the presence of a stoichiometric quantity of a tertiary amine, such as triethylamine to react with the hydrogen chloride which is generated by the reaction. The resulting triethylamine hydrochloride can be filtered off. The filtrate containing the desired product is then vacuum-stripped to remove the benzene and the residue obtained is crystallized from benzene-diethyl ether (1:1 v/v) to yield the desired product The physiologically or pharmacologically acceptable acid addition salts of the compounds of the present invention are included within this invention. These acid addition salts are prepared by known processes, such as illustrated in several of the preceding examples, which involve reacting a free base compound of the present invention with an appropriate acid in a suitable solvent, for example, diethyl ether or ethyl alcohol. For example, among the mineral acids that can be used to prepare the subject acid addition salts are hydrochloric acid, hydrobromic acid, sulfuric acid, and phosphoric acid Suitable organic acids that can be used to prepare the subject acid addition salts are, for example, acetic acid, methanesulfonic acid, propionic acid, maleic acid, fumaric acid, tartaric acid, citric acid, and benzoic acid As shown in the above examples, the compounds of the present invention can be suitably purified by conventional methods, for example, by distillation, crystallization, or chromatography as indicated.

The acyl chloride reactants used to prepare the products of the present invention represented by formula (a) herein above where R is an acyl radical or substituted acyl radical can readily be prepared from their corresponding acid compound by reaction with an excess of a suitable agent, such as thionyl chloride or phosphorus halides, such as $PCl_3$ and $PCl_5$. All of the acyl chloride reactants required for the preparation of the subject substituted compounds can be prepared by suitably using one of the well-known methods illustrated in Examples A to J. However, most of the acyl chlorides needed to prepare the subject compounds are commercially available.

EXAMPLE A

Salicylyl Chloride

A mixture of 10 grams of salicylic acid, 7 ml of thionyl chloride and 0.02 grams of aluminum chloride were heated at 40°–45° C. for 1.5 hours. The excess thionyl chloride was removed in vacuum and salicylyl chloride was obtained.

EXAMPLE B

Nicotinoyl Chloride-Hydrochloride

A mixture of 90 grams of nicotinic acid and 180 ml of thionyl chloride were heated at 55°–65° C. for 3.5 hours. The excess thionyl chloride was removed in vacuum and nicotinoyl chloride-hydrochloride was obtained

EXAMPLE C m-Methoxybenzoyl Chloride

A mixture of 50 grams of m-methoxybenzoic acid and 125 ml of thionyl chloride were heated for 3 hours at 70° C. The excess thionyl chloride was stripped under vacuum to yield the desired acyl chloride product. The product m-methoxybenzoyl chloride distilled at 77°–78° C./1-2 mm Hg.

The procedure used to prepare m-methoxybenzoyl chloride (Example C) was employed to synthesize the acyl chlorides listed in Table IV. The molar ratio of thionyl chloride to acid reactant used, for example, can be within the range of 2:1 to 4:1. The exact amount of thionyl chloride used is not critical so long as it is in substantial molar excess in relation to the acid reactant. After the desired reaction is complete, the excess thionyl chloride is easily removed by stripping under vacuum.

cies being treated, particular disorder being treated, weight of the animal, and the route of administration. In accordance with the present invention, the subject compounds are administered at doses from about 1.0 milligram to 600 milligrams per kilograms body weight 1 to 4 times a day. A more preferred dose is from about 2.0 milligrams to 400 milligrams per kilogram body weight 1 to 4 times a day.

The analgesic and anti-inflammatory properties of the novel compounds of the present invention were determined by several different testing procedures. Among the tests used are, for example, the Rat Inflamed Paw Pressure Test, the Mouse Acetylcholine Writhing Test, and the Rat Carrageenan Edema Test, which can be carried out as follows:

Rat Inflamed Paw Pressure Test (Analgesic Test)

Non-fasted albino rats in the weight range of 160 to 180 grams are used. The experimental drugs are administered orally 10 ml/kg volume). Immediately after the administration, 0.1 ml of a 1% sodium carrageenan (Marine Colloids, Inc., Springfield, N.J.) in a sterile 0.9% aqueous solution of sodium chloride is injected into the subplantar region of the right hind paw. At a specific time post drug administration, the animal's right hind paw is placed between two plastic-grooved discs which are compressed by air pressure, and the amount of pressure required to induce vocalization and/or biting of the apparatus is recorded. The average pressure requirements for a drug-treated group of 6 animals is compared to that of a control group which received 0.9% saline in place of the drug. The percent change of the test group from the control group is calculated.

3-Benzoyl-8-oxa-3-azabicyclo(3.2.1)octane when evaluated in this test had an $ED_{50}$ of 315 mg/kg body weight. Acetylsalicyclic acid in the same test had an $ED_{50}$ of 1,500 mg/kg body weight, and codeine sulfate had an $ED_{50}$ of 167 mg/kg body weight. 3-Phenylacetyl-8-oxa-3-azabicyclo(3.2.1)octane when evaluated in this test had an $ED_{50}$ of 220 mg/kg body weight.

Mouse Acetylcholine Writhing Test (Analgesic Test)

Female albino mice weighing 18 to 25 grams are administered the test drugs orally (10 ml/kg volume). One-half hour after administration of the test drug, acetylcholine bromide (11.0 ml/kg) is administered intraperitoneally (10 ml/kg) and the time to writhing recorded. The observation period extended for 10 min-

TABLE IV

| Example | Acid Reactants | Acyl Chloride Products | Boiling Point |
|---|---|---|---|
| D | o-chlorophenylacetic acid | o-chlorophenylacetyl chloride | (1) |
| E | m-chlorophenylacetic acid | m-chlorophenylacetyl chloride | (2) |
| F | p-chlorophenylacetic acid | p-chlorophenylacetyl chloride | 85°C./1.0 mm Hg |
| G | o-tolylacetic acid | o-tolylacetyl chloride | (2) |
| H | m-tolylacetic acid | m-tolylacetyl chloride | (2) |
| I | p-tolylacetic acid | p-tolylacetyl chloride | (2) |
| J | o-acetoxybenzoic acid | o-acetoxybenzoyl chloride | 75.5–76°C./0.04 mm Hg |

(1) The o-chlorophenyl acetic acid and thionyl chloride were heated at 110°C. for 3 hours and the product used without further purification.
(2) The excess thionyl chloride was removed under vacuum and the product was used without any further purification.

Evaluation in laboratory animals indicates that the present compounds possess analgesic and/or anti-inflammatory activity when administered in a therapeutically effective amount. The effectiveness and dosage required vary, as is customary in this art, with the speutes. Control animals dosed with 0.9% saline (10 mg/kg) are tested simultaneously. The percent inhibition of writhing is calculated from the number that did not writhe in 5 minutes post injection of the acetylcholine bromide.

3-Benzoyl-8-oxa-3-azabicyclo(3.2.1)octane when evaluated in this test had an $ED_{50}$ of 500 mg/kg body weight. Acetylsalicylic acid in the same test had an $ED_{50}$ of 150 mg/kg body weight and codeine sulfate had an $ED_{50}$ of 46 mg/kg body weight. 3-Phenylacetyl-8-oxa-3-azabicyclo(3.2.1)octane when evaluated in this test had an $ED_{50}$ of 195 mg/kg body weight. 3-(m-Chlorobenzoyl)-8-oxa-3-azabicyclo(3.2.1)octane when evaluated in this test had an $ED_{50}$ of 460 mg/kg body weight.

Rat Carrageenan Edema Test (Anti-inflammatory Test)

Non-fasted albino rats in the weight range of 160 to 180 grams are used. The test drugs are administered orally. Immediately following administration of the drug, 0.1 ml of a 1% carrageenan suspension (Marine Colloids, Inc., Springfield, N.J.) in a sterile 0.9% aqueous solution of sodium chloride is injected into the subplantar area of the right hind paw and the foot volume measured by volume displacement. The foot volume is measured again at 4 hours post injection of the drug and the percent change in volume when compared to a control group receiving 0.9% saline instead of the drug is calculated.

3-Phenylacetyl-8-oxa-3-azabicyclo(3.2.1)octane when evaluated in this test had an $ED_{50}$ of 550 mg/kg body weight. Acetylsalicylic acid in this test had an $ED_{50}$ of 110 mg/kg body weight. Codeine sulfate exhibited no activity in this test 3-Benzoyl-8-oxa-3-azabicyclo(3.2.1)octane when evaluated in this test had an $ED_{50}$ of 600 mg/kg body weight.

The designation $ED_{50}$ is used hereinabove to designate a dose level which showed significant activity in 50% of the animals tested.

As the compounds within the scope of this invention are effective upon oral administration, they can be compounded into any suitable oral dosage form, such as in tablet, capsule, syrup, elixir, suspension or other solid or liquid forms that can be prepared by procedure well known in the art. Thus, the subject novel compounds can be mixed with a suitable diluent, such as lactose or kaolin, and encapsulated; or they can be combined with suitable binding agents and expanding agents and compressed into tablets. In addition, a liquid pharmaceutical may be obtained by dissolving, dispersing, or suspending novel compounds of this invention with a suitable flavored liquid. The present compounds are also considered active upon parenteral and rectal administration.

Examples of formulations for preparing tablets, capsules, liquids, parenterals, and suppositories containing the compounds of the present invention are described below. Obviously, it will be recognized by one skilled in the present art that the following formulations represent only one method of preparing such pharmaceutical compositions and obviously the size of the tablet or capsule or the strength of the dosage form may be suitably varied in order to satisfy the particular requirements, such as dosage level indicated. For example, each dosage unit may conveniently contain from about 15 milligrams to 5,000 milligrams of the active ingredient admixed with a diluent amount of a pharmaceutically acceptable carrier. Any of the well-known suitable pharmaceutical carriers can be used to prepare acceptable dosage forms so as to provide an effective amount or therapeutically effective amount of the compound to be administered.

Suppository Containing 250 mg of 8-Oxa-3-Azabicyclo(3.2.1)Octane

| | |
|---|---|
| 8-Oxa-3-Azabicyclo(3.2.1)Octane | 0.250 gram |
| Cocoa Butter | 1.750 grams |
| Make of Such No. 100 | |

Melt the cocoa butter and disperse the 8-oxa-3-azabicyclo(3.2.1)octane into the molten mass and stir until uniform. Pour the resulting molten mass into a suppository mold and chill. Remove suppositories from mold and package.

Suspension Containing 100 mg per 5 cc of 3-Benzoyl-8-Oxa-3-Azabicyclo(3.2.1)Octane

| | |
|---|---|
| 3-Benzoyl-8-Oxa-3-Azabicyclo(3.2.1)Octane | 20 grams |
| Tragacanth | 50 grams |
| Amaranth | 10 grams |
| Syrup Wild Cherry | 60 ml |
| Distilled Water, q.s. | 1000 ml |

Hydrate the tragacanth with sufficient water to form a smooth paste and to this add the 3-benzoyl-8-oxa-3-azabicyclo (3.2.1)octane, followed by the amaranth which has been previously dissolved in water. Then add the syrup of wild cherry and distilled water to make 1000 ml.

Capsule Containing 250 mg of 3,3'-Hexamethylene-Bis[8-Oxa-3-Azabicyclo(3.2.1)Octane]

| | |
|---|---|
| 3,3'-Hexamethylene-Bis[8-Oxa-3-Azabicyclo (3.2.1)Octane] | 250 mg |
| Powdered Lactose | 100 mg |
| D.T.D. Capsules No. 1000 | |

Mix the ingredients so as to evenly distribute the active ingredient throughout the lactose. Pack the powder into a No. 1 empty gelatin capsule.

Tablet Containing 200 mg of 3-(2-Guanadinoethyl)-8-Oxa-3-Azabicyclo(3.2.1)Octane Hydrosulfate Monohydrate

| | |
|---|---|
| 3-(2-Guar dinocthyl)-8-Oxa-3-Azabicyclo (3.2.1) Octane hydrosulfate Monohydrate | 200 grams |
| Starch | 80 grams |
| Powdered Lactose | 80 grams |
| Talc | 20 grams |
| Weight of Granulation | 380 grams |

Combine all ingredients, mix, and then compress into slugs. The slugs should then be ground to form granules that will pass through a 14 to 16 mesh screen. The granules may then be recompressed into 1000 tablets using a suitable compression mold to form tablets, each weighing 380 mg.

Injectable Containing 10 mg of 3-(o-Toluoyl)-8-Oxa-3-Azabicyclo(3.2.1) Octane Per Milliliter Suitable for Intramuscular, Intraperitoneal or Subcutaneous Injection

| | |
|---|---|
| 3-(o-Toluoyl)-8-Oxa-3-Azabicyclo (3.2.1)Octane | 10.0 grams |
| Chlorobutanol | 3.0 grams |
| Propylene Glycol | 40.0 ml |
| Water for Injection, q.s. | 1000.0 ml |

Combine the above ingredients, clarify by filtration, fill into vials, seal, and autoclave.

Having thus described my invention, I claim:

1. An analgesic composition comprising a pharmaceutical carrier and an analgesically effective amount of a compound represented by the formula

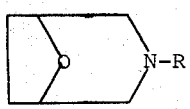

wherein R is a radical selected from the group consisting of benzyl; phenyl; aminoalkyl ($C_1$ to $C_6$); dimethylaminoalkyl ($C_1$ to $C_6$); phenylacetyl; quinoxaloyl; mono-, di-, or tri-alkoxy ($C_1$ to $C_4$) substituted benzoyl; phenylalkyl where the alkyl constituent thereof contains from 1 to 4 carbon atoms; alkenyl ($C_3$); mono-, di-, or tri-halogen substituted phenylalkyl where the alkyl group contains from 1 to 4 carbon atoms and the halogen is substituted on the phenyl ring; guanadinoalkyl ($C_1$ to $C_4$); mono-, di-, or tri-halogen substituted benzoyl; di- or tri-alkyl ($C_1$ to $C_4$) substituted benzoyl; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylalkanoyl wherein the alkanoyl group contains from 2 to 4 carbon atoms; o- and p-alkyl ($C_1$ to $C_4$) substituted phenylalkanoyl where the alkanoyl group contains 2 to 4 carbon atoms and the alkyl group is substituted on the phenyl ring; alkyl ($C_1$ to $C_4$) substituted naphthylalkanoyl wherein the alkanoyl group contains 2 to 4 carbon atoms and the alkyl group or groups are attached to the naphthyl ring; alkanoyl ($C_4$ to $C_{18}$); haloalkyl ($C_1$ to $C_4$) mono-, di-, or tri-substituted benzoyl wherein the haloalkyl group contains from 1 to 5 halogen atoms; mono-, di-, or tri-alkoxy ($C_1$ to $C_4$) substituted phenylalkyl wherein the alkyl group contains 1 to 4 carbon atoms and the alkoxy is substituted on the phenyl ring; thienylalkyl wherein the alkyl group contains from 1 to 4 carbon atoms; anilinocarbonyl; adamantanecarbonyl; phenylsulfonyl; mono- or di-carboxyl substituted benzoyl; mono- or di-hydroxyl substituted benzoyl; nicotinoyl; mono- or di- alkanoyloxy ($C_2$ to $C_4$) substituted benzoyl; thenoyl; phenylglyoxylyl; cycloalkyl ($C_4$ to $C_8$); N-(alkylene α,ω-dicarbonyl)-8-oxa-3-azabicyclo(3.2.1)octane; N-(alkylene-8-oxa-3-azabicyclo(3.2.1)octane; and N-(terephthaloyl)-8-oxa-3-azabicyclo(3.2.1) octane; or the pharmacologically acceptable acid addition salts thereof.

2. An analgesic composition of claim 1 wherein R is a radical selected from the group consisting of benzyl, N-(hexamethylene)-8-oxa-3-azabicyclo(3.2.1)octane, phenyl, aminohexyl, phenylacetyl, quinoxaloyl, m-methoxybenzoyl, α-methylphenethyl, aminoethyl, propenyl, α-methyl p-chlorophenethyl, dimethylaminopropyl, phenethyl, 2-guanadinoethyl, p-chlorobenzoyl, m-chlorobenzoyl, o-chlorobenzoyl, m-chlorophenylacetyl, p-chlorophenylacetyl, N-(ethylene)-8-oxa-3-azabicyclo(3.2.1)octane, α-methylphenethyl, α, α-dimethylphenethyl, p-chlorophenethyl, hexahydrobenzoyl, ochlorophenylacetyl, cinnamoyl, phenethylcarbonyl, o-methylphenylacetyl, heptanoyl, m-trifluoromethylbenzoyl, p-methoxyphenethyl, α-methyl- thienylethyl, anilinocarbonyl, adamantanecarbonyl, phenylsulfonyl, o-carboxybenzoyl, stearoyl, o-hydroxybenzoyl, nicotinoyl, o-acetoxybenzoyl, thenoyl, phenylglyoxylyl, cyclohexyl, and 3,4-dimethoxyphenethyl, or the pharmacologically acceptable acid salts thereof.

3. An analgesic composition comprising a pharmaceutical carrier and an analgesically effective amount of a compound represented by the formula

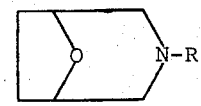

wherein R is a radical selected from the group consisting of benzyl; phenyl; phenylacetyl; quinoxaloyl; mono-, di-, or tri-alkoxy ($C_1$ to $C_4$) substituted benzoyl; phenylalkyl where the alkyl constituent thereof contains from 1 to 4 carbon atoms; mono-, di-, or tri-halogen substituted phenylalkyl where the alkyl group contains from 1 to 4 carbon atoms and the halogen is substituted on the phenyl ring; guanadinoalkyl ($C_1$ to $C_4$); mono-, di-, or tri-halogen substituted benzoyl; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylalkanoyl wherein the alkanoyl group contains from 2 to 4 carbon atoms; o- and p-alkyl ($C_1$ to $C_4$) substituted phenylalkanoyl where the alkanoyl group contains 2 to 4 carbon atoms and the alkyl group is substituted on the phenyl ring; alkyl ($C_1$ to $C_4$) substituted naphthylalkanoyl wherein the alkanoyl group contains 2 to 4 carbon atoms and the alkyl group or groups are attached to the naphthyl ring; haloalkyl ($C_1$ to $C_4$) mono-, di-, or tri-substituted benzoyl wherein the haloalkyl group contains from 1 to 5 halogen atoms; mono-, di-, or tri-alkoxy ($C_1$ to $C_4$) substituted phenylalkyl wherein the alkyl group contains 1 to 4 carbon atoms and the alkoxy is substituted on the phenyl ring; thienylalkyl wherein the alkyl group contains from 1 to 4 carbon atoms; anilinocarbonyl; adamantanecarbonyl; phenylsulfonyl; mono- or di-carboxyl substituted benzoyl; mono- or di-hydroxyl substituted benzoyl; nicotinoyl; mono- or dialkanoyloxy ($C_2$ to $C_4$) substituted benzoyl; thenoyl; phenylglyoxylyl; and cycloalkyl ($C_4$ to $C_8$) or the pharmacologically acceptable acid addition salts thereof.

4. An analgestic composition comprising a solid pharmaceutical carrier and an analgesically effective amount of 3-benzoyl-8-oxa-3-azabicyclo(3.2.1)octane.

5. An analgesic composition comprising a solid pharmaceutical carrier and an analgesically effective amount of 8-oxa-3-azabicyclo(3.2.1)octane or a pharmacologically acceptable acid addition salt thereof.

6. An analgesic composition comprising a solid pharmaceutical carrier and an analgesically effective amount of 3-alkyl($C_1$ to $C_6$)-8-oxa-3-azabicyclo(3.2.1) octane or a pharmacologically acceptable acid addition salt thereof.

7. An analgesic composition comprising a solid pharmaceutical carrier and an analgesically effective amount of 3-acetyl-8-oxa-3-azabicyclo(3.2.1)octane.

8. A method of alleviating pain in an animal comprising administering to said animal an analgesically effective amount of a compound represented by the following formula

wherein R is a radical selected from the group consisting of benzyl; phenyl; aminoalkyl ($C_1$ to $C_6$); dimethylaminoalkyl ($C_1$ to $C_6$); phenylacetyl; quinoxaloyl; mono-, di-, or tri-alkoxy ($C_1$ to $C_4$) substituted benzoyl; phenylalkyl where the alkyl constituent thereof contains from 1 to 4 carbon atoms; alkenyl ($C_3$); mono-, di-, or tri-halogen substituted phenylalkyl where the alkyl group contains from 1 to 4 carbon atoms and the halogen is substituted on the phenyl ring; guanadionalkyl ($C_1$ to $C_4$); mono-, di-, or tri-halogen substituted benzoyl; di- or tri-alkyl ($C_1$ to $C_4$) substituted benzoyl; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylalkanoyl wherein the alkanoyl group contains from 2 to 4 carbon atoms; o- and p-alkyl ($C_1$ to $C_4$) substituted phenylalkanoyl where the alkanoyl group contains 2 to 4 carbon atoms and the alkyl group is substituted on the phenyl ring; alkyl ($C_1$ to $C_4$) substituted naphthylalkanoyl wherein the alkanoyl group contains 2 to 4 carbon atoms and the alkyl group or groups are attached to the naphthyl ring; alkanoyl ($C_4$ to $C_{18}$); haloalkyl ($C_1$ to $C_4$) mono-, di-, or tri-substituted benzoyl wherein the haloalkyl group contains from 1 to 5 halogen atoms; mono-, di-, or tri-alkoxy ($C_1$ to $C_4$) substituted phenylalkyl wherein the alkyl group contains 1 to 4 carbon atoms and the alkoxy is substituted on the phenyl ring; thienylalkyl wherein the alkyl group contains from 1 to 4 carbon atoms; anilinocarbonyl; adamantanecarbonyl; phenylsulfonyl; mono- or di-carboxyl substituted benzoyl; mono- or di-hydroxyl substituted benzoyl; nicotinoyl; mono- or di-alkanoyloxy ($C_2$ to $C_4$) substituted benzoyl; thenoyl; phenylglyoxylyl; cycloalkyl ($C_4$ to $C_8$); N-(alkylene α,ω-dicarbonyl)-8-oxa-3-azabicyclo(3.2.1)octane; N-(alkylene-8-oxa-3azabicyclo(3.2.1)octane; and N-(terephthaloyl)-8-oxa-3-azabicyclo(3.2.1)octane; or the pharmacologically acceptable acid addition salts thereof.

9. A method of alleviating pain in an animal comprising administering to said animal an analgesically effective amount of a compound represented by the formula

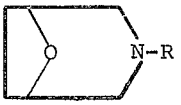

wherein R is a radical selected from the group consisting of benzyl; phenyl; phenylacetyl; quinoxaloyl; mono-, di-, or trialkoxy ($C_1$ to $C_4$) substituted benzoyl; phenylalkyl where the alkyl constituent thereof contains from 1 to 4 carbon atoms; mono-, di-, or tri-halogen substituted phenylalkyl where the alkyl group contains from 1 to 4 carbon atoms and the halogen is substituted on the phenyl ring; quanadinoalkyl ($C_1$ to $C_4$); mono-, di-, or tri-halogen substituted benzoyl; mono-, di-, or tri-halogen substituted phenylalkanoyl wherein the alkanoyl group contains from 2 to 4 carbon atoms and the halogen is on the phenyl ring; hexahydrobenzoyl; phenylalkenoyl wherein the alkenoyl group is a lower alkenoyl containing from 3 to 5 carbon atoms; phenylalkanoyl wherein the alkanoyl group contains from 2 to 4 carbon atoms; o- and p- alkyl ($C_1$ to $C_4$) substituted phenylalkanoyl where the alkanoyl group contains 2 to 4 carbon atoms and the alkyl group is substituted on the phenyl ring; alkyl ($C_1$ to $C_4$) substituted naphthylalkanoyl wherein the alkanoyl group contains 2 to 4 carbon atoms and the alkyl group or groups are attached to the naphthyl ring; haloalkyl ($C_1$ to $C_4$) mono-, di-, or trisubstituted benzoyl wherein the haloalkyl group contains from 1 to 5 halogen atoms; mono-, di-, or tri-alkoxy ($C_1$ to $C_4$) substituted phenylalkyl wherein the alkyl group contains 1 to 4 carbon atoms and the alkoxy is substituted on the phenyl ring; thienylalkyl wherein the alkyl group contains from 1 to 4 carbon atoms; anilinocarbonyl; adamantanecarbonyl; phenylsulfonyl; mono- or di-carboxyl substituted benzoyl; mono- or di-hydroxyl substituted benzoyl; nicotinoyl; mono- or di-alkanoyloxy ($C_2$ to $C_4$) substituted benzoyl; thenoyl; phenylglyoxylyl; and cycloalkyl ($C_4$ to $C_8$) or the pharmacologically acceptable acid addition salts thereof.

10. A method of alleviating pain in an animal comprising administering to said animal an analgesically effective amount of a compound represented by the formula

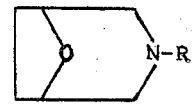

wherein R is a radical selected from the group consisting of benzyl, N-(hexamethylene)-8-oxa-3-azabicyclo(3.2.1)octane, phenyl, aminohexyl, phenylacetyl, quinoxaloyl, m-methoxybenzoyl, α-methylphenethyl, aminoethyl, propenyl, α-methyl p-chlorophenethyl, dimethylaminopropyl, phenethyl, 2-guanadinoethyl, p-chlorobenzoyl, m-chlorobenzoyl, o-chlorobenzoyl, m-chlorophenylacetyl, p-chlorophenylacetyl, N-(ethylene)-8-oxa-3-azabicyclo(3.2.1)octane, β-methylphenethyl, β,β-dimethylphenethyl, p-chlorophenethyl, hexahydrobenzoyl, o-chlorophenylacetyl, cinnamoyl, phenethylcarbonyl, o-methylphenylacetyl, heptanoyl, m-trifluoromethylbenzoyl, p-methoxyphenethyl, α-methylthienylethyl, anilinocarbonyl, adamantanecarbonyl, phenylsulfonyl, o-carboxybenzoyl, stearoyl, o-hydroxybenzoyl, nicotinoyl, o-acetoxybenzoyl, thenoyl, phenylglyoxylyl, cyclohexyl, and 3,4-dimethoxyphenethyl, or the pharmacologically acceptable acid addition salts thereof.

11. A method of alleviating pain in an animal comprising administering to said animal an analgesically effective amount of 3-benzoyl-8-oxa-3-azabicyclo(3.2.1)octane.

12. A method of alleviating pain in an animal comprising administering to said animal an anagesically effective amount of 8-oxa-3-azabicyclo(3.2.1)octane or a pharmacologically acceptable acid addition salt thereof.

13. A method of alleviating pain in an animal comprising administering to said animal an analgesically effective amount of 3-alkyl($C_1$ to $C_6$)-8-oxa-3-azabicyclo(3.2.1)octane or a pharmacologically acceptable acid addition salt thereof.

14. A method of alleviating pain in an animal comprising administering to said animal an analgesically effective amount of 3-acetyl-8-oxa-3-azabicyclo(3.2.1)octane.

* * * * *

UNITED STATES PATENT AND TRADEMARK OFFICE
CERTIFICATE OF CORRECTION

PATENT NO. : 3,953,596
DATED : April 27, 1976
INVENTOR(S) : Alfred D. Miller

Page 1 of 2

It is certified that error appears in the above-identified patent and that said Letters Patent are hereby corrected as shown below:

Column 3, line 5, "3-benzoyl-8oxa-3-azabicyclo(3.2.1)octane" should read -- 3-benzoyl-8-oxa-3-azabicyclo(3.2.1)octane --.

Column 5, line 4, "3(p-" should read -- 3-(p- --.

Column 5, line 26, After the word "present" and before the word "is" insert the word -- invention --.

Column 6, line 65, "NCl" should read -- HCl --.

Column 9, Table I, Example 12, "Cinnamoyl chloride" should read -- Cinnamoyl chloride* --.

Column 14, line 6, "3-Phenylclyoxlyl-8-Oxa-3-Azabicyclo(3.2.1)Octane" should read -- 3-Phenylglyoxylyl-8-Oxa-3-Azabicyclo(3.2.1)Octane --.

Column 16, line 55, After the words "dimethyl ether" insert -- ) --.

Column 19, Table III, Example 51, "205-205-207°C" should read -- 205-207°C --.

Column 26, line 20, Before "10 ml/kg" insert -- ( --.

Column 28, line 46, "3-(2-Guar dinocthyl)-8-Oxa-3-Azabicyclo" should read -- 3-(2-Guanadinoethyl)-8-Oxa-3-Azabicyclo --.

Column 29, line 51, "(alkylene-8-oxa-3-azabicyclo(3.2.1)octane" should read -- (alkylene)-8-oxa-3-azabicyclo(3.2.1)octane --.

UNITED STATES PATENT AND TRADEMARK OFFICE
CERTIFICATE OF CORRECTION

PATENT NO. : 3,953,596
DATED : April 27, 1976
INVENTOR(S) : Alfred D. Miller

It is certified that error appears in the above-identified patent and that said Letters Patent are hereby corrected as shown below:

Column 29, line 64, "α-methylphenethyl, α,α-" should read -- β-methylphenethyl, β,β- --.

Column 31, line 46, "(alkylene-8-oxa-3azabicyclo(3.2.1)octane" should read -- (alkylene)-8-oxa-3-azabicyclo(3.2.1)octane --.

Signed and Sealed this second Day of August 1977

[SEAL]

Attest:

RUTH C. MASON
Attesting Officer

C. MARSHALL DANN
Commissioner of Patents and Trademarks